US012083158B2

(12) United States Patent
Bond et al.

(10) Patent No.: US 12,083,158 B2
(45) **Date of Patent: *Sep. 10, 2024**

(54) ANTIBACTERIAL COMPOSITIONS, METHODS OF MAKING AND USE THEREOF

(71) Applicant: MOREHOUSE SCHOOL OF MEDICINE, Atlanta, GA (US)

(72) Inventors: Vincent Craig Bond, Stone Mountain, GA (US); Michael Powell, Douglasville, GA (US); Ming Bo Huang, Atlanta, GA (US); Syed Ali, New Iberia, LA (US); Martin N. Shelton, Seattle, WA (US)

(73) Assignee: Morehouse School of Medicine, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,242

(22) Filed: Dec. 19, 2018

(65) Prior Publication Data

US 2019/0134151 A1 May 9, 2019

Related U.S. Application Data

(63) Continuation-in-part of application No. 15/397,359, filed on Jan. 3, 2017, now Pat. No. 10,206,974, which is a continuation of application No. 14/156,119, filed on Jan. 15, 2014, now Pat. No. 9,556,224, which is a continuation of application No. 13/267,977, filed on Oct. 7, 2011, now Pat. No. 8,669,226.

(60) Provisional application No. 62/678,002, filed on May 30, 2018.

(51) Int. Cl.

| | |
|---|---|
| *A61K 38/00* | (2006.01) |
| *A61K 38/08* | (2019.01) |
| *A61K 38/16* | (2006.01) |
| *A61K 45/06* | (2006.01) |
| *A61K 47/60* | (2017.01) |
| *A61K 47/64* | (2017.01) |
| *C07K 7/06* | (2006.01) |
| *C07K 14/005* | (2006.01) |
| *C12N 7/00* | (2006.01) |

(52) U.S. Cl.
CPC ............ *A61K 38/162* (2013.01); *A61K 38/08* (2013.01); *A61K 45/06* (2013.01); *A61K 47/60* (2017.08); *A61K 47/6455* (2017.08); *C07K 7/06* (2013.01); *C07K 14/005* (2013.01); *C12N 7/00* (2013.01); *C07K 2319/10* (2013.01); *C12N 2740/16032* (2013.01); *C12N 2740/16322* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 8,071,540 | B2 | 12/2011 | Montelaro et al. | |
| 8,431,530 | B2 | 4/2013 | Bond et al. | |
| 8,476,237 | B2 | 7/2013 | Bond et al. | |
| 8,551,943 | B2 | 10/2013 | Bond et al. | |
| 8,563,506 | B2 | 10/2013 | Bond et al. | |
| 8,669,226 | B2 | 3/2014 | Bond et al. | |
| 9,556,224 | B2 | 1/2017 | Bond et al. | |
| 2006/0140911 | A1 | 6/2006 | Sharp et al. | |
| 2007/0055049 | A1 | 3/2007 | Grey et al. | |
| 2008/0057038 | A1 | 3/2008 | Yacoby et al. | |
| 2008/0286210 | A1 * | 11/2008 | He .......................... | A61K 8/64 424/45 |
| 2009/0149673 | A1 * | 6/2009 | Zhang .................. | C07C 229/26 562/553 |
| 2010/0061932 | A1 | 3/2010 | Brock et al. | |
| 2010/0317566 | A1 | 12/2010 | Bond et al. | |
| 2010/0322929 | A1 | 12/2010 | Zurawski et al. | |
| 2011/0020290 | A1 | 1/2011 | Soothill et al. | |
| 2011/0046008 | A1 | 2/2011 | Love et al. | |
| 2011/0319593 | A1 | 12/2011 | Ensoli et al. | |

(Continued)

FOREIGN PATENT DOCUMENTS

| | | |
|---|---|---|
| WO | 2013/052058 | 4/2013 |
| WO | 2016/177900 | 11/2016 |

(Continued)

OTHER PUBLICATIONS

Zhu, W.L. et al., "Effects of dimerization of the cell-penetrating peptide Tat analog on antimicrobial activity and mechanism of bactericidal action", Journal of Peptide Science, 2009, vol. 15(5), pp. 345-352.
Ahmad, A. et al., "Identification and design of antimicrobial peptides for therapeutic applications", Current Protein and Peptide Science, 2012, vol. 13(3), pp. 211-223.
International Search Report and the Written Opinion of International Application No. PCT/US2019/033967 mailed Oct. 3, 2019.
Morris, et al., "A Peptide Carrier for the Delivery of Biologically Active Proteins into Mammalian Cells: Application to the Delivery of Antibodies and Therapeutic Proteins", Nature Biotechnology, vol. 19, pp. 1173-1176 (2001).
Joliot, et al., "Transduction peptides: from technology to physiology", Nature Cell Biology, vol. 6, No. 3, pp. 189-196 (2004).
Heitz, et al., "Twenty years of cell-penetrating peptides: from molecular mechanisms to therapeutics", British Journal of Pharmacology, vol. 157, pp. 195-206 (2009).

(Continued)

*Primary Examiner* — Maury A Audet
(74) *Attorney, Agent, or Firm* — Ping Wang; Kalos Athena Wang PLLC

(57) ABSTRACT

Compositions and methods for reducing the growth of and/or preventing the formation of a microbial biofilm are disclosed. The composition comprises an antimicrobial SMR peptide comprising an HIV-1 SMRwt peptide and a cell penetrating peptide (CPP) domain. In some embodiments, the composition further comprises one or more other antimicrobial peptides (AMPs), antibiotics, matrix-inhibiting compounds, matrix-disaggregating compounds, quorum sensing inhibitors, or a combination thereof. In other embodiments, the compositions are used for impregnating or coating an article and/or material surface with the composition to render it less prone to microbial infections.

5 Claims, 14 Drawing Sheets

Specification includes a Sequence Listing.

(56) References Cited

U.S. PATENT DOCUMENTS

| | | | |
|---|---|---|---|
| 2012/0289454 A1* | 11/2012 | Cowan | C07H 23/00 514/2.3 |
| 2013/0018002 A1 | 1/2013 | Bond et al. | |
| 2013/0018003 A1 | 1/2013 | Bond et al. | |
| 2013/0089525 A1* | 4/2013 | Bond | A61K 38/08 424/93.6 |
| 2013/0123202 A1 | 5/2013 | Bond et al. | |
| 2013/0150809 A1 | 6/2013 | Whiteford et al. | |
| 2014/0155319 A1 | 6/2014 | Bond et al. | |
| 2017/0209533 A1 | 7/2017 | Bond et al. | |
| 2018/0170969 A1 | 6/2018 | Bond et al. | |
| 2018/0258148 A1* | 9/2018 | Bames | C07K 14/4702 |
| 2019/0134151 A1 | 5/2019 | Bond et al. | |
| 2019/0135873 A1 | 5/2019 | Bond et al. | |
| 2019/0167759 A1 | 6/2019 | Bond et al. | |

FOREIGN PATENT DOCUMENTS

| | | |
|---|---|---|
| WO | 2018118015 | 6/2018 |
| WO | 2020013879 | 1/2020 |

OTHER PUBLICATIONS

Yacoby, et al., "Targeting Antibacterial Agents by Using Drug-Carrying Filamentous Bacteriophages", Antimicrobial Agents and Chemotherapy (AAC), vol. 50, No. 6, pp. 2087-2097 (2006).

Yacoby, et al. "Targeted Drug-Carrying Bacteriophages as Antibacterial Nanomedicines", Antimicrobial Agents and Chemotherapy (AAC), vol. 51, No. 6, pp. 2156-2163 (2007).

Proft, "Sortase-mediated protein ligation: an emerging biotechnology tool for protein modification and immobilisation", Biotechnol Lett, vol. 32, pp. 1-10 (2010).

Ali, S.A., et al., "Genetic Characterization of HIV Type 1 Nef-Induced Vesicle Secretion", Aids Research and Human Retroviruses, vol. 26, No. 2, pp. 173-192 (2010).

http://en.wikipedia.org/wiki/Polymyxin, last updated Oct. 26, 2014.

File History of U.S. Appl. No. 15/397,359, filed Jan. 3, 2017.

File History of U.S. Appl. No. 14/156,119, filed Jan. 15, 2014.

File History of U.S. Appl. No. 13/267,977, filed Oct. 7, 2011.

Extended European Search Report of Application No. 19810419.2 mailed Feb. 9, 2022.

* cited by examiner

| SMRwt-CPPtat Peptide: H2N-SMRwt-CPPtat-OH |

H2N-VGFPVAAVGFPV-GRKKRRQRRRPPQ-OH [SEQ ID NO: 9]

H2N - [SEQ ID NO: 3] – [SEQ ID NO: 8] - OH

| SMRmut-CPPtat Peptide: H2N-SMRmut-CPPtat-OH |

H2N-AGFPVAAAGFPV-GRKKRRQRRRPPQ-OH [SEQ ID NO: 11]

H2N - [SEQ ID NO: 10] – [SEQ ID NO: 8] - OH

```
                            SEQUENCE LISTING

<160> NUMBER OF SEQ ID NOS: 11

<210> SEQ ID NO 1
<211> LENGTH: 5
<212> TYPE: PRT
<213> ORGANISM: Human immunodeficiency virus

<400> SEQUENCE: 1

Val Gly Phe Pro Val
1               5

<210> SEQ ID NO 2
<211> LENGTH: 5
<212> TYPE: PRT
<213> ORGANISM: Simian immunodeficiency virus

<400> SEQUENCE: 2

Val Gly Val Ser Val
1               5

<210> SEQ ID NO 3
<211> LENGTH: 12
<212> TYPE: PRT
<213> ORGANISM: Human immunodeficiency virus

<400> SEQUENCE: 3

Val Gly Phe Pro Val Ala Ala Val Gly Phe Pro Val
1               5                   10

<210> SEQ ID NO 4
<211> LENGTH: 12
<212> TYPE: PRT
<213> ORGANISM: ARTIFICIAL SEQUENCE
<220> FEATURE:
<223> OTHER INFORMATION: Synthetic

<400> SEQUENCE: 4

Val Gly Val Ser Val Ala Ala Val Gly Val Ser Val
1               5                   10

<210> SEQ ID NO 5
<211> LENGTH: 20
<212> TYPE: PRT
<213> ORGANISM: ARTIFICIAL SEQUENCE
<220> FEATURE:
<223> OTHER INFORMATION: Synthetic

<400> SEQUENCE: 5

Val Gly Phe Pro Val Ala Ala Val Gly Phe Pro Val Asp Tyr Lys Asp
1               5                   10                  15

Asp Asp Asp Lys
            20

<210> SEQ ID NO 6
<211> LENGTH: 8
<212> TYPE: PRT
<213> ORGANISM: ARTIFICIAL SEQUENCE
<220> FEATURE:
<223> OTHER INFORMATION: Synthetic

<400> SEQUENCE: 6
```

```
Asp Tyr Lys Asp Asp Asp Asp Lys
1               5

<210> SEQ ID NO 7
<211> LENGTH: 20
<212> TYPE: PRT
<213> ORGANISM: ARTIFICIAL SEQUENCE
<220> FEATURE:
<223> OTHER INFORMATION: Synthetic

<400> SEQUENCE: 7

Ala Gly Phe Pro Val Ala Ala Ala Gly Phe Pro Val Asp Tyr Lys Asp
1               5                  10                  15

Asp Asp Asp Lys
            20

<210> SEQ ID NO 8
<211> LENGTH: 13
<212> TYPE: PRT
<213> ORGANISM: Human immunodeficiency virus

<400> SEQUENCE: 8

Gly Arg Lys Lys Arg Arg Gln Arg Arg Arg Pro Pro Gln
1               5                  10

<210> SEQ ID NO 9
<211> LENGTH: 25
<212> TYPE: PRT
<213> ORGANISM: ARTIFICIAL SEQUENCE
<220> FEATURE:
<223> OTHER INFORMATION: Synthetic

<400> SEQUENCE: 9

Val Gly Phe Pro Val Ala Ala Val Gly Phe Pro Val Gly Arg Lys Lys
1               5                  10                  15

Arg Arg Gln Arg Arg Arg Pro Pro Gln
            20                  25

<210> SEQ ID NO 10
<211> LENGTH: 12
<212> TYPE: PRT
<213> ORGANISM: ARTIFICIAL SEQUENCE
<220> FEATURE:
<223> OTHER INFORMATION: Synthetic

<400> SEQUENCE: 10

Ala Gly Phe Pro Val Ala Ala Ala Gly Phe Pro Val
1               5                  10

<210> SEQ ID NO 11
<211> LENGTH: 25
<212> TYPE: PRT
<213> ORGANISM: ARTIFICIAL SEQUENCE
<220> FEATURE:
<223> OTHER INFORMATION: Synthetic

<400> SEQUENCE: 11

Ala Gly Phe Pro Val Ala Ala Ala Gly Phe Pro Val Gly Arg Lys Lys
1               5                  10                  15

Arg Arg Gln Arg Arg Arg Pro Pro Gln
            20                  25
```

ANTIBACTERIAL COMPOSITIONS, METHODS OF MAKING AND USE THEREOF

This application claims priority of U.S. Provisional Application Ser. No. 62/678,002, filed May 30, 2018. This application also a continuation-in-part of U.S. application Ser. No. 15/397,359, filed Jan. 3, 2017, which is a continuation of U.S. application Ser. No. 14/156,119, filed Jan. 15, 2014, now U.S. Pat. No. 9,556,224, which is a continuation of U.S. application Ser. No. 13/267,977, filed Oct. 7, 2011, now U.S. Pat. No. 8,669,226. The entireties of the aforementioned applications are incorporated herein by reference.

This application was made with government support under certain grants awarded by NIH. The government has certain rights in the application.

FIELD

The present application relates generally to compositions and method for medical treatment and, in particular, to antimicrobial compositions and method for treating microbial infections.

BACKGROUND

Microorganisms can live and proliferate as individual cells swimming freely in the environment (e.g., plankton), or they can grow as highly organized, multicellular communities encased in a self-produced polymeric matrix in close association with surfaces and interfaces. The latter microbial lifestyle is referred to as a biofilm. Biofilm formation represents an ancient, protected mode of growth that allows microbial survival in hostile environments and allows microorganisms to disperse and colonize new niches. In their natural habitats, microorganisms predominantly grow in biofilms attached to either an abiotic or a biotic surface, such that the biofilms form highly structured communities embedded in a self-produced extracellular polymeric substance (EPS), which is a polymeric conglomeration generally, composed of extracellular DNA, proteins, and polysaccharides.

The composition of biofilms is complex and variable among different microbial species and even within the same species under different environmental conditions. Nonetheless, biofilm formation represents the normal lifestyle of microorganism in the environment and all microbes can make biofilms, which are highly structured communities embedded in a self-produced matrix.

Bacteria within a biofilm display phenotypes and possess properties that are markedly different from those of the same group growing planktonically, including a dramatically reduced susceptibility (up to 1000 times) to conventional antibiotics compared to their planktonic counterparts. This accounts for a high rate of treatment failure and persistence of many types of biofilm infections, particularly those caused by various multidrug resistant bacteria, such as the methicillin/oxacillin-resistant *Staphylococcus aureus* (MRSA), vancomycin-resistant enterococci (VRE), and penicillin-resistant *Streptococcus pneumonia* (PRSP). Further, at least two-thirds of all clinical infections are biofilm-associated. Accordingly, there is great interest in developing new strategies for dealing with biofilm-associated infections.

Most organisms produce gene encoded antimicrobial peptides (AMPs) as innate defenses to prevent colonization and infection by multiple microbial pathogens. As such, AMPs are a form of "nature's antibiotics" and have been the subject of intense research development, particularly against drug resistant microorganisms. AMPs have varying microbial specificities, cellular targets, modes of action, potencies, and adverse side effects against mammalian cells. Many of the AMPs under development suffer from weak activity, non-specific cytotoxicity, susceptibility to proteolysis, inability to control intracellular microbial infections. Accordingly, there is a need for new and effective AMPs and methods for their use.

SUMMARY

The inventors of the present application have surprisingly discovered a novel AMP, comprising an HIV-1 secretion modulation region (SMR), which has antimicrobial activity and is capable of disrupting biofilms. This AMP was initially identified as an HIV-1 Nef-derived antagonist of Mortalin that disrupts HIV-1 Nef's interaction with mortalin and blocks virus and Nef exosome release (J Virol. 2012 January; 86(1): 406-19).

In one embodiment, the present application provides a composition comprising an antimicrobial SMR peptide, wherein the antimicrobial SMR peptide comprises an HIV-1 SMRwt peptide and a cell penetrating peptide (CPP) domain. In a particular embodiment, the antimicrobial SMR peptide comprises an amino acid sequence set forth in SEQ ID NO: 9. In certain embodiments, the composition further comprises one or more other antimicrobial peptides (AMPs), antibiotics, matrix-inhibiting compounds, matrix-disaggregating compounds, quorum sensing inhibitors, or combinations thereof.

In another aspect, the present application provides an item impregnated with, coated in or covered by the antimicrobial SMR of the present application, alone or in combination with one or more other antimicrobial peptides (AMPs), antibiotics, matrix-inhibiting compounds, matrix-disaggregating compounds, quorum sensing inhibitors, or combinations thereof, wherein the item is selected from the group consisting of a medical device, medical instrument, medical implement, prosthetic, implantable device or material or tissue and wound dressing. In some embodiments, the item includes a plastics or metal surface impregnated with, coated in or covered with the antimicrobial SMR peptide.

In another aspect, the SMR peptide and/or other active agents are incorporated in a biologically compatible material selected from the group consisting of paint, glue, cement, composite, tissue matrix, tissue scaffold or wound dressing.

In another aspect, the SMR peptide and/or other active agents are incorporated in a dental preparation, wherein the dental preparation comprises a spray, mouthwash, gel, paste, lozenge or chewing gum.

In another aspect, a method for treating a microbial infection comprises administering a therapeutically effective amount of a pharmaceutical composition comprising the SMR peptide of the present application, alone or in combination with the other active agents described herein.

In one embodiment, the subject is infected with a *Staphylococcus* species.

In another embodiment, the subject is infected with a bacterium selected from the group consisting of methicillin-resistant *Staphylococcus aureus* (MRSA), *Staphylococcus epidermidis*, and vancomycin-resistant *Enterococcus* (VRE).

In another embodiment, the infection is an oral or dental infection.

In another embodiment, the pharmaceutical composition is administered to a wound.

In another aspect, a method of detaching a microorganism from a surface or from other microorganisms comprises contacting the microorganism with a composition comprising the SMR peptide of the present application, alone or in combination with the other active agents described herein.

In another aspect, a method for reducing the growth and/or preventing the formation of a microbial biofilm comprises contacting a material, liquid, surface or biological material with an effective amount of a composition comprising the antimicrobial SMR of the present application, alone or in combination with the other active agents described herein.

In a further aspect, a method for dispersing a biofilm in water or detaching biofilm formation from a surface, comprises treating water with or coating the surface with the antimicrobial SMR of the present application, alone or in combination with the other active agents described herein.

These and other objects, aspects, and embodiments will become more apparent when read with the following detailed description and drawings.

Figure 1:
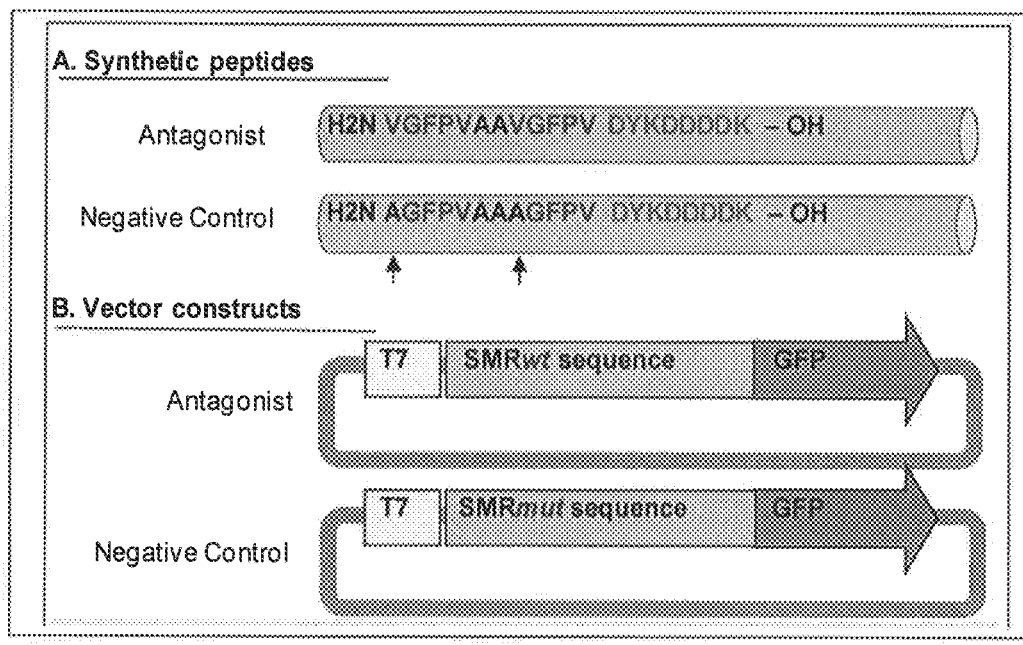
FIG. 1 is a composite of diagrams showing a synthetic HIV-I Nef SMRwt peptide (SEQ ID NO: 5) and HIV-1 Nef SMRmut peptide (SEQ ID NO:7, negative control) (panel A); the vector constructs expressing HIV-1 Nef SMRwt peptide fused with GFP or HIV-1 Nef SMRmut peptide fused with GFP (panel B). In both synthetic peptide and vector, the SMRwt or SMRmut sequences are identical. There are two SMR motifs in the synthetic peptides while only one in the vector constructs. Arrows show site of amino acid changes in SMRmut motifs.

While the present disclosure will now be described in detail, and it is done so in connection with the illustrative embodiments, it is not limited by the particular embodiments illustrated in the figures and the appended claims.

DETAILED DESCRIPTION

The invention and accompanying drawings will now be discussed in reference to the numerals provided therein so as to enable one skilled in the art to practice the present invention. The skilled artisan will understand, however, that the inventions described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

It will be appreciated that reference throughout this specification to aspects, features, advantages, or similar language does not imply that all of the aspects and advantages may be realized with the present invention should be or are in any single embodiment of the invention. Rather, language referring to the aspects and advantages is understood to mean that a specific aspect, feature, advantage, or characteristic described in connection with an embodiment is included in at least one embodiment of the present invention. Thus, discussion of the aspects and advantages, and similar language, throughout this specification may, but do not necessarily, refer to the same embodiment.

The described aspects, features, advantages, and characteristics of the invention may be combined in any suitable manner in one or more further embodiments. Furthermore, one skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention.

Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

Definitions

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. Further, it should be understood that where a given range is described in the present application, the range should be understood to additionally include any other range defined by any combination of integer values encompassed by the given range.

As used herein, the term "SMR peptide" refers to an HIV-I Nef secretion modulation region (SMR) peptide comprising one or more copies of the VGFPV (SEQ ID NO: 1) motif. In certain embodiments, the SMR peptide further includes a cell penetrating peptide (CPP) domain or other functional domains for enhancing the anti-microbial or anti-biofilm properties of the compositions described herein.

As used herein, the term "CPP domain" refers to functional domain for promoting uptake into eukaryotic cells of peptides or proteins joined to or associated therewith.

As used herein, the phrase "microbial infection" refers to an infection caused by bacteria, fungi and/or protozoans.

As used herein, the term "bacteria" refers to members of a large group of unicellular microorganisms that have cell walls but lack organelles and an organized nucleus.

As used herein, the term "Gram-positive bacteria" to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus* spp., *Bifidobacterium* spp., *Clostridium* spp., *Clostridium* spp., *Corynebacterium* spp., *Enterococcus* spp., *Erysipelothrix* spp., *Eubacterium* spp., *Gardnerella* spp., *Gemella* spp., *Leuconostoc* spp., *Mycobacterium* spp., *Nocardia* spp., *Peptococcus* spp., *Peptostreptococcus* spp., *Proprionibacterium* spp., *Sarcina* spp., *Staphylococcus* spp., and *Streptococcus* spp.

As used herein, the term "MRSA" refers to gram-positive bacterium methicillin-resistant *Staphylococcus aureus* (MRSA). The term MRSA encompasses any strain of *S. aureus* that has developed, through horizontal gene transfer and natural, multiple drug resistance to beta-lactam antibiotics.

As used herein, the term "Gram-negative bacteria" refers to bacteria characterized by the presence of a double membrane surrounding each bacterial cell. Representative Gram-negative bacteria include *Acinetobacter* spp., *Actinobacillus* spp., *Aggregatibacter* spp., *Aeromonas* spp., *Alcaligenes* spp., *Bacteroides* spp., *Bartonella* spp., *Bordetella* spp., *Borrelia* spp., *Branhamella* spp., *Brucella* spp., *Campylobacter* spp., *Chlamydia* spp., Chromobacterium spp., *Citrobacter* spp., *Eikenella* spp., *Enterobacter* spp., *Escherichia* spp., *Flavobacterium* spp., *Fusobacterium* spp., *Haemophilus* spp., *Helicobacter* spp., *Klebsiella pneumoniae, Klebsiella* spp., *Legionella* spp., *Leptospira* spp., *Moraxella* spp., *Morganella* spp., *Mycoplasma* spp., *Neisseria* spp., *Pasteurella* spp., *Plesiomonas* spp., *Prevotella* spp., *Proteus* spp., *Providencia* spp., *Pseudomonas* spp., *Rickettsia* spp., *Rochalimaea* spp., *Salmonella* spp., *Salmonella* spp., *Serratia* spp., *Shigella* spp., *Treponema* spp., *Veillonella* spp., *Vibrio* spp., and *Yersinia* spp.

As used herein, the term "fungi" refers to heterotrophic organisms characterized by the presence of a chitinous cell wall, and in the majority of species, filamentous growth as multicellular hyphae. Representative fungi whose adhesion may be prevented according to the method of the present application include *Candida albicans, Saccharomyces cerevisiae, Candida glabrata. Candida parapsilosis* and *Candida dubliniensis*.

As used herein, the term "protozoan" refers to any member of a diverse group of eukaryotes that are primarily unicellular, existing singly or aggregating into colonies, are usually nonphotosynthetic, and are often classified further into phyla according to their capacity for and means of motility, as by pseudopods, flagella, or cilia. Exemplary protozoans include, but are not limited to *Plasmodium* species, including *P. falciparum, P. vivax, P. ovale*, and *P. malariae; Leishmania* species, including *L. major, L. tropica, L. donovani, L. infantum, L. chagasi, L. mexicana, L. panamensis, L. braziliensis* and *L. guyanensi; Cryptosporidium, Isospora belli, Toxoplasma gondii, Trichomonas vaginalis*, and *Cyclospora* species.

As used herein, the term "biofilm" refers to a sessile community of microorganisms characterized by cells that are attached to a substratum or interface or to each other, that are embedded in a matrix of extracellular polymers (more specifically extracellular polymers that they have produced), and that exhibit an altered phenotype with respect to growth rate and gene transcription (for example as, compared to their "non-biofilm", free-floating or planktonic counterparts).

Unless otherwise noted, the term "detach" refers to removal a single cell organism, in vitro or in vivo, from a surface to which the cell is adhered (e.g., by reducing the rate of growth on a surface) or removing the cell from other single cell organisms to which they are adhered. Preferably, the compositions of the present application are capable of detaching cells from adherence by as much as 10%, more preferably by 20%, more preferably by 30%, more preferably by 40%, more preferably by 50%, more preferably by 60%, more preferably by 70%, more preferably by 80%, more preferably by 90% and most preferably by 100% as measured by an adhesion assay.

"Detachment" of a biofilm occurs when a single or cluster of cell organisms in the biofilm detaches from a surface; "dispersion" of a biofilm occurs when single cell organisms in a biofilm detach from each other.

As used herein, the term "contacting" refers to the positioning of a composition of the present application so that it is in direct or indirect contact with one or more microorganisms such that the active agents in the composition are able to effect the growth properties of the one or more microorganisms. Thus, the present application contemplates both applying the compositions of the present application to a desirable surface and/or directly to the adhesive cells. Contacting the compositions with a surface can be effected using any method known in the art including spraying, spreading, wetting, immersing, dipping, painting, ultrasonic welding, welding, bonding or adhering. The compositions of the present application may be attached as monolayers or multiple layers.

As used herein the term "medical device" refers to any implant, instrument, apparatus, implement, machine, device or any other similar or related object (including any component or accessory), which is intended for use in the diagnosis, treatment, cure or prevention of disease or other conditions.

As used herein, the term "implant" refers to any object intended for placement in a human body that is not a living tissue. The implant may be temporary or permanent. An implant can be a medical device or article comprising artificial components, such as catheters or pacemakers. Implants can also include naturally derived objects that have been processed so that their living tissues have been devitalized. As an example, bone grafts may be processed so that their living cells are removed (acellularized), but so that their shape is retained to serve as a template for ingrowth of bone from a host. As another example, naturally occurring coral can be processed to yield hydroxyapatite preparations that can be applied to the body for certain orthopedic and dental therapies.

As used herein, the term "antimicrobial peptide", "AMP", and "bacteriocin" are used interchangeably with reference to any synthetic or naturally occurring protein- or peptide-like substance having microbicidal activity against bacteria, viruses, fungi, yeasts, mycoplasma, protozoa or combinations thereof. The antimicrobial peptide may be a member of the RNAse A super family, a defensin, cathelicidin, granulysin, histatin, psoriasin, dermicidine or hepcidin. The antimicrobial peptide may be naturally occurring in insects, fish, plants, arachnids, vertebrates or mammals. As used herein, the AMP or bacteriocin may be produced by a microorganism or to by a synthetic and/or genetic engineering process, and refers to both wild-type and modified forms of the parent bacteriocin that have been altered by insertion or deletion of one or more amino acid residues.

The term "anti-biofouling agent" refers to the compound or substance used to protect underwater surfaces from attaching single cell organisms. These single cell organisms include microorganism such as bacteria and fungi.

The term "pharmaceutically acceptable carrier" refers to a carrier or a diluent that does not cause significant irritation to an organism and does not abrogate the biological activity and properties of the administered compound. An adjuvant is included under these phrases.

The Antimicrobial SMR Peptide

One aspect of the present application relates to a method for treating a microbial infection, comprising: administering to a subject in need of such treatment an effective amount of an antimicrobial SMR peptide comprising a first antimicrobial domain comprising at least one VGFPV (SEQ ID NO: 1) motif or at least one VGVSV (SEQ ID NO: 2) motif, or an effective amount of an expression vector that encodes the antimicrobial SMR peptide and expresses the antimicrobial SMR peptide in the subject.

The antimicrobial SMR peptide can be of various lengths. In certain embodiments, the antimicrobial SMR peptide has a length of 10-200 amino acids, 10-100 amino acids or 10-50 amino acids and comprises at least one VGFPV (SEQ ID NO: 1) motif. In other embodiments, the antimicrobial SMR peptide comprises at least two VGFPV (SEQ ID NO: 1) motifs In certain other embodiments, the antimicrobial SMR peptide comprises 2, 3, 4, 5, 6, 7, 8 or more VGFPV (SEQ ID NO: 1) motifs. In other embodiments, the antimicrobial SMR peptide comprises at least one VGFPV (SEQ ID NO: 1) motif at the N-terminal. In other embodiments, the antimicrobial SMR peptide comprises at least one VGFPV (SEQ ID NO: 1) motif at the C-terminal. In other embodiments, the antimicrobial SMR peptide comprises the amino acid sequence of VGFPVAAVGFPV (SEQ ID NO: 3). In other embodiments, the antimicrobial SMR peptide comprises at least one VGVSV (SEQ ID NO: 2) motif. In other embodiments, the antimicrobial SMR peptide comprises at least two VGVSV (SEQ ID NO: 2) motifs. In other embodiments, the antimicrobial SMR peptide comprises at least one VGFPV (SEQ ID NO: 1) motif and at least one VGVSV (SEQ ID NO: 2) motif. In yet other embodiments, the antimicrobial SMR peptide comprises the amino acid sequence of VGVSVAAVGVSV (SEQ ID NO: 4).

In other embodiments, the antimicrobial SMR peptide of the present application is further modified to include a second antimicrobial domain comprising a known AMP sequence. Alternatively, the antimicrobial SMR peptide can be included in a composition along with one or more other AMPs. The inclusion of other AMPs further enhances and/or synergizes with the antimicrobial activity of the antimicrobial SMR peptide of the present application and/or facilitates the uptake of the antimicrobial SMR peptide by the microorganism. Examples of known AMPs or their synthetic derivatives include, but are not limited to, andropin, apidaecin, bacteriocin leucocin A, bactenecin, bactenecin-7, buforin II, cathelicidin LL-37, clavanin A, cecropin, cecropin A-magainin 2 hybrid peptide, dermcidin-1L, cyclic dodecapeptide, β-defensin I, α-defensin (HNP-1), DJK-5, DJK-6, E3-APO, gaegurin, histatin, histatin-5, indolicidin, IDR-1018, magainin 2, melittin B, nisin A, novispirin G10, pyrrhocoricin, protegrin, protegrin PG-1, ranalexin, tachyplesin-1, as well as structurally-related analogs therefrom.

In some embodiments, the AMP or bacteriocin is capable of degrading bacterial cell walls, such as lyostaphin (degrading *Staphylococcus* cell walls), mutanolysin (degrading *Streptococcus* cell walls) and enterolysin (degrading *Enterococcus* cell walls). The killing ability of bacteriocins is considered a successful strategy for maintaining population and reducing the numbers of competitors to obtain more nutrients and living space in environments.

In other embodiments, the antimicrobial SMR peptide of the present application further comprises a cell penetrating peptide (CPP) domain. A CPP domain enhances the uptake of the antimicrobial SMR peptide of the present application by a eukaryotic cell. This is particularly important with regard controlling the growth and/or spread of intracellular microbial pathogens. Exemplary CPP domains for use in the present application include, but are not limited to, HIV $TAT_{49-57}$ peptide, HIV $TAT_{48-60}$ peptide (SEQ ID NO: 8), low molecular weight protamine (LMWP) peptide; Chariot™, also known as Pep-I (Morris et al., Nat. Biotechnol., 19:1173-1176, 2001); $Antp_{43-58}$ peptide, MPG (HIV Gp41-SV40 NLS), SAP, MPG R9, MAP, K-FGF, Penetratin, Buforin II, Transportan, Ku70, Prion, pVEC, Pep-1-K, Pep-7, HN-1, TP10, and CP26 (See e.g., Joliot et al., Nature Cell Biol., 6(3): 189-196, 2004 and Heitz et al., Br. *J. Pharmacol.,* 157:195-206, 2009).

In other embodiments, the antimicrobial SMR peptide of the present application further comprises a targeting domain. The targeting domain allows the antimicrobial SMR peptide of the present application to be targeted to one or more desired microorganisms of interest. In a specific embodiment, the targeting domain comprises an antibody-derived epitope binding domain or other cellular ligand capable of binding to a surface molecule of the microorganism of interest.

Exemplary epitope binding domains include, but not limited to a member of the group consisting of: IgG, antibody variable region; isolated CDR region; single chain Fv molecule (scFv) comprising VH and VL domain linked by a peptide linker allowing for association between the two domains to form an antigen binding site; bispecific scFv dimer; minibody comprising a scFv joined to a CH3 domain, single chain diabody fragment, dAb fragment, which consists of a VH or a VL domain; Fab fragment consisting of VL, VH, CL and CH1 domains; Fab' fragment, which differs from a Fab fragment by the addition of a few residues at the carboxyl terminus of the heavy chain CH1 domain, including one or more cysteines from the antibody hinge region; Fab'-SH fragment, which is a Fab' fragment in which the cysteine residue(s) of the constant domains bear a free thiol group; F(ab')2, bivalent fragment comprising two linked Fab fragments; Fd fragment consisting of VH and CH1 domains; derivatives thereof, and any other antibody fragment(s) retaining antigen-binding function. Fv, scFv, or diabody molecules may be stabilized by the incorporation of disulphide bridges linking the VH and VL domains. Preferably, the epitope binding domain is selected to target and specifically bind to an antigen expressed on the surface of a particular target microorganism of interest.

In other embodiments, the targeting domain comprises a cell surface receptor-binding ligand or cell-binding peptide isolated from a phage display library, for example. Phage display libraries engineered for binding cell surface molecules or receptors are well known to those of skill in the art.

The antimicrobial SMR peptide of the present application may contain one or more targeting domains. When using a plurality, the targeting domains may be the same or different. In addition the one or more targeting domain(s) may be further linked to an Fc region. The Fc region can facilitate recruitment of Fc receptor-bearing natural killer cells, macrophages, neutrophils, and mast cells, which can stimulate phagocytic or cytotoxic cells to destroy microbes or infected cells by antibody-mediated phagocytosis or antibody-dependent cell-mediated cytotoxicity. Further, when using antibody-derived targeting agents, any or all of the targeting domains therein and/or Fc regions may be "humanized" using methodologies well known to those of skill in the art.

In certain embodiments, the antimicrobial SMR peptide of the present application further comprises one or more spacers or linkers that link different domains, such as the first and the second antimicrobial domains, the CPP domain and the targeting domain, within the antimicrobial SMR peptide. The spacer or linker is designed to facilitate the independent folding of each domain relative to one another and ensure that the individual domains in the peptide do not interfere with one another or with the SMR peptide. The spacer may include any amino acid or mixtures thereof. In one embodiment, the spacer comprises between 1 to 50 amino acids, preferably 3 to 10 amino acids in length.

Preferably, the spacer will be designed to increase the flexibility of the protein and facilitate adoption of an extended conformation. For example, the spacer may have a high glycine content to force the spacer to adopt a loop conformation. Glycine is favored for use in spacers because the absence of a B-carbon permits the polypeptide backbone to access dihedral angles that are energetically forbidden for other amino acids. In addition, spacers comprising glycine and/or serine have a high freedom degree for linking of two peptides, i.e., they enable the fused proteins to fold and produce functional proteins. Preferably, the spacer comprises hydrophilic residues enhancing stability and folding of the fusion protein, and will include other residues other than glycine, such as, for example, alanine or serine. Preferred peptide spacers are comprised of the amino acids proline, lysine, glycine, alanine, and/or serine, and combinations thereof. In one embodiment, the linker is a glycine rich linker. In a particular embodiment, the spacer having the formula $[(Gly)_n\text{-Ser/Ala}]_m$ where n is from 1 to 4, inclusive, and m is from 1 to 4, inclusive.

The antimicrobial SMR peptide of the present application may be chemically modified using one or more methods including, but not limited to, amidation, acetylation (including N-terminal acetylation), carboxylation, glycosylation, methylation (e.g., substitution of α-hydrogens with methyl groups), carbonylation, phosphorylation, PEGylation, dimerization, addition of interchain and/or intrachain disulfide bonds, addition of trans olefin, derivatization by known protecting/blocking groups, circularization, substitution with D amino acids, linkage to an antibody molecules or other cellular ligands, etc.

Additional modifications include, for example, point mutations, insertions, deletion, truncation, and backbone substitutions, such as NH to NCH$_3$, In addition, the peptide may be modified by the insertion of one or more D amino acids. Further, proline analogs in which the ring size of the proline residue is changed from 5 members to 4, 6, or 7 members can be employed. Cyclic groups can be saturated or unsaturated, and if unsaturated, can be aromatic or non-aromatic In one embodiment, the antimicrobial SMR peptide comprises a modified C-terminus and/or a modified N-terminus. For example, the N-terminus can be acetylated (Ac) and/or the C-terminus can be amidated (NH$_2$). Where the C-terminus is amidated, the carboxylic acid of the amino acid is converted to an amide, i.e., NH$_2$-CH2-C(O)—NH$_2$.

The antimicrobial SMR peptide may further contain one or more covalently attached functional groups, preferably attached to either or both of the N and C termini of the polypeptide. These covalently attached groups can include stabilizers, couplers, ligands, enzymatic substrates and/or combinations thereof. Preferred groups include acyl groups on the N terminus and cysteamine (cya) coupling groups on the C terminal end. To the latter may be conveniently attached other chemical moieties, e.g., dyes, ligands, proteins, enzymes, enzymatic substrates, etc. Alternatives to cya are also known to those of skill in the art. For stabilizing and/or blocking, e.g., cya may be replaced with an alky group such as methyl or ethyl, which are known to be conveniently positioned onto a —COOH group.

N-terminal modifications additionally include, but are not limited to, methylating (i.e., —NHCH3 or —NH(CH3)2), adding a 1-amino-cyclohexane-carboxylic acid moiety (Chex); and adding a carbobenzoyl group, or blocking the amino terminus with any blocking group containing a carboxylate functionality defined by RCOO—, where R is selected from the group consisting of naphthyl, acridinyl, steroidyl, and similar groups.

A derivitizing group, including, but not limited to, a sulfhydryl-containing group or moiety may be positioned at the C-terminus of the AMFP, even when it is not coupled to another chemical moiety. In one embodiment, the C-terminal end may be modified with a cysteamide group (—NH—CH2—CH2—SH), which can allow further coupling to drugs. A cysteamide group is compatible with the peptide synthesis using the Fmoc strategy and leads to a C-terminal protected peptide. Alternatively, the peptide can include a C-terminal cysteine residue containing a sulfhydryl (—SH) group that can be optionally utilized for conjugation to other moieties. In another embodiment, the C-terminal end includes a 2,4-diamino-butyric acid (DAB) moiety. C-terminal modifications may further include replacing the free acid with a carboxamide group or forming a cyclic lactam at the carboxy terminus to introduce structural constraints.

Naturally occurring side chains of the 20 genetically encoded amino acids (or D amino acids) may be replaced with other side chains with similar properties, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic.

Such substitutions can include but are not necessarily limited to: (1) non-standard positively charged amino acids, like: ornithine; N-(4-aminobutyl)-glycine having a lysine side chain attached to the "N-terminus" and aminopropyl or aminoethyl groups attached to the amino group of glycine; (2) Non-naturally occurring amino acids with no net charge and sidechains similar to arginine, such as citrulline, with or without methylene groups; (3) non-standard non-naturally occurring amino acids with OH (e.g., serine), such as, homoserine, hydroxyproline, hydroxyvaline, and penicillamin; (4) proline derivatives, such as, D-Pro, including 3,4-dehydroproline, pyroglutamine, proline with fluorine substitutions on the ring, 1,3-thiazolidine-4-carboxylic acid; (5) Histidine derivative, such as beta-(2-thienyl)-alanine; or (6) alkyl derivatives, such as 2-aminobutyric acid, norvaline, norleucine, homoleucine, and alpha-aminoisobutyric acid.

In another embodiment, the C-terminal carboxyl group or a C-terminal ester may be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH2C12), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

In other embodiments, the antimicrobial SMR peptide of the present application is cyclized or includes a desamino or descarboxy residue at the peptide termini so that there are no terminal amino or carboxyl groups. This can decrease susceptibility to proteases and/or to restrict the conformation of the peptide. C-terminal functional groups of the compounds of the present application include amide, amide lower alkyl, amide di(lower alkyl), lower alkoxy, hydroxy, and carboxy, and the lower ester derivatives thereof, and the pharmaceutically acceptable salts thereof. The antimicrobial SMR peptide may be cyclized by adding an N and/or C terminal cysteine and cyclizing the peptide through disulfide linkages or other side chain interactions.

In some embodiments, the antimicrobial SMR peptide of the present application are synthesized using traditional liquid- or solid-phase synthesis. Fmoc and t-Boc solid phase peptide synthesis (SPPS) can be employed to grow the peptides from carboxy to amino-terminus. In certain embodiments, the last "amino acid" added to the reaction is PEGylated. This last amino acid is often referred to as a carboxyl-PEG-amine, carboxyl-PEO-amine, or amine-PEG-acid, whereby the amine is blocked to protect against reaction and the acid is free to react with the amine group from the previously added amino acid in the reaction. PEG (polyethylene glycol) and PEO (polyethylene oxide) are polymers composed of repeating subunits of ethylene glycol and ethylene oxide monomers. In one embodiment, the PEG moiety is 5 to 30 kDa in size. In another embodiment, the PEG moiety is 10 to 20 kDa in size.

In addition to using PEGylated end amino acid during synthesis, the antimicrobial SMR peptide of the present application may be PEGylated by PEGylation. PEGylation is the process of covalent attachment of polyethylene glycol polymer chains to another molecule, normally a drug or therapeutic protein. PEGylation can be achieved by incubation of a reactive derivative of PEG with the antimicrobial SMR peptide or AMP. The covalent attachment of PEG to an antimicrobial peptide can "mask" the antimicrobial peptide from the host's immune system (reduced immunogenicity and antigenicity), increase the hydrodynamic size (size in solution) of the antimicrobial peptide which prolongs its circulatory time by reducing renal clearance. PEGylation can also provide water solubility to hydrophobic proteins.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used as a site specific site by conjugation with aldehyde functional polymers.

In certain embodiments, the PEG derivatives are produced by reacting the PEG polymer with a group that is reactive with hydroxyl groups, typically anhydrides, acid chlorides, chloroformates and carbonates. In other embodiments, more efficient functional groups such as aldehyde, esters, amides, etc. are made available for protein conjugation.

In certain embodiments, heterobifunctional PEGs are used for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters. In other embodiments, the pegylation agents contain branched, Y shaped or comb shaped polymers that show reduced viscosity and lack of organ accumulation. Any other enhancers of pharmacokinetics (PK) and/or pharmacodynamics (PD) may also be used In other embodiments, the antimicrobial SMR peptides of the present application are linked to transferrin or siderophores, such as pesticin, that bind to receptors on bacteria surface.

Treatment or Prevention of Microbial Infections

An antimicrobial agent, such as the antimicrobial SMR peptide of the present application, has the capacity to kill, disrupt the reproduction of, inhibit the growth of, or reduce the drug-resistance of a microorganism.

In certain embodiments, the antimicrobial SMR peptide is used for the treatment or prevention of bacterial infection. Exemplary bacteria include, but are not limited to Mycobacterium species, including *M. tuberculosis*; Staphylococcus species, including *S. aureus*, methicillin-resistant *S. aureus* (MRSA), *S. epidermidis*, *S. saprophyticus*, *S. xylosus*, *S. lugdunensis*, *S. schleiferi*, *S. caprae*, *S. hominis*, *S. saprophyticus*, *S. warneri*; Streptococcus species, including *S. pneumoniae*, *S. pyogenes*, *S. mutans*, *S. epidermidis*, *S. agalactiae*, *S. equi*, *S. canis*, *S. bovis*, *S. equimuis*, *S. anginosus*, *S. sanguis*, *S. salivarius*, *S. mitis*; other pathogenic *Streptococcal* species, including *Enterococcus* species, such as *E. faecalis* and *E. faecium*, including Vancomycin-resistant *Enterococci* (VRE) strains thereof; *Lactobacillus* species, such as *L. plantarum* and *L. lactis*; *Haemophilus influenza*, *Pseudomonas* species, including *P. aeruginosa*, *P. pseudomallei*, and *P. mallei*, *Salmonella* species, including *S. enterocolitis*, *S. typhimurium*, *S. enteritidis*, *S. bongori*, and *S. choleraesuis*; *Shigella* species, including *S. flexneri*, *S. sonnei*, *S. dysenteriae*, and *S. boydii*, *Brucella* species, including *B. melitensis*, *B. suis*, *B. abortus*, and *B. pertussis*; *Neisseria* species, including *N. meningitidis* and *N. gonorrhoeae*; *Escherichia coli*, including enterotoxigenic *E. coli* (ETEC); *Vibrio cholerae*, *Helicobacter pylori*, *Chlamydia trachomatis*, *Clostridium difficile* (C. Diff), *Cryptococcus neoformans*, *Moraxella* species, including *M. catarrhalis*, *Campylobacter* species, including *C. jejuni*; *Corynebacterium* species, including *C. diphtheriae*, *C. ulcerans*, *C. pseudotuberculosis*, *C. pseudodiphtheriticum*, *C. urealyticum*, *C. hemolyticum*, *C. equi*, *Listeria monocytogenes*, *Nocardia asteroides*, *Pasteurella multocida*, *Bacteroides* species, *Actinomycetes* species, *Treponema pallidum*, *Leptospirosa* species, *Klebsiella pneumoniae*; *Proteus* sp., including *Proteus vulgaris*; *Serratia* species, *Acinetobacter*, *Yersinia* species, including *Y. pestis* and *Y. pseudotuberculosis*; *Francisella tularensis*, *Enterobacter* species, *Bacteroides* species, *Legionella* species, *Borrelia burgdorferi*, and the like.

In other embodiments, the antimicrobial SMR peptide is used for the treatment or prevention of fungi infections. Exemplary fungi for treatment include, but are not limited to, *Aspergillus* species. *Dermatophytes*, *Blastomyces derinatitidis*, *Candida* species, including *C. albicans* and *C. krusei*; *Malassezia furfur*, *Exophiala werneckii*, *Piedraia hortai*, *Trichosporon beigelii*, *Pseudallescheria boydii*, *Madurella grisea*, *Histoplasma capsulatum*, *Sporothrix schenckii*, *Histoplasma capsulatum*, *Tinea* species, including *T. versicolor*, *T. pedis T. anguium*, *T. cruris*, *T. capitus*. *T. corporis*, *T. barbae*; *Trichophyton* species, including *T.* rubrum, *T. interdigitale, T. tonsurans, T. violaceum, T. yaoundei. T. schoenleinii, T. megninii, T. soudanense, T. equiman, T. erinacei*, and *T. verrucosum:* Microsporum species, including *M. audouini, M. ferrugineum, M. canis, M. nanum, M. distortum, M. gypseum, M. fulvum*, and the like.

In other embodiments, the antimicrobial SMR peptide is used for the treatment or prevention of protozoan infections, such as infections by Cryptosporidium, *Isospora belli, Toxoplasma gondii, Trichomonas vaginalis*, and Cyclospora species.

In other embodiments, the antimicrobial SMR peptide may be useful for treating or preventing a variety of conditions including, for example, infections of the skin (e.g., *Eethyma gangrdenosum*, infections of the urogenital tract, infections of the digestive system (e.g., the gut), infections of the lung, and/or infections of the sinus. For example, the antimicrobial compositions may be useful for the treatment of a condition, such as, for example, rosacea, atopic dermatitis (e.g., eczema), a *Candida* infection (e.g., vaginal, diaper, intertrigo, balanitis, oral thrush), *Tinea versicolor, Dermatophytosis* (e.g., *Tinea pedis* (athlete's foot)), Tinea unguium, Onychomycosis (e.g., toe nail fungus), *Tinea cruris, Tinea capitus, Tinea corporis, Tinea barbae*, seborrheic dermatitis, antibiotic-resistant skin infections, impetigo, ecthyma, erythrasma, burn wounds (e.g., reduction of infections, improved healing), diabetic foot/leg ulcers (e.g., reduction of infections, improved healing), prevention of central catheter-related blood stream infections, oral mucositis, warts (e.g., common, flat, plantar, genital), and molluscum contagiosum. In some embodiments, the condition is acne, often acne vulgaris and sometimes acne conglobate.

Route and Dose of Antimicrobial SMR Peptide Administration

The antimicrobial SMR peptide of the present application may be administered orally, intrathecally, intra-arterially, intravenously, intradermally, subcutaneously, transdermally (topically) or transmucosally. An antimicrobial composition may be administered by any route, including oral, rectal, pulmonary, sublingual, and parenteral administration. Parenteral administration includes, for example, intraperitoneal, intravenous, intramuscular, intraarterial, intravesical (e.g., to the bladder), intradermal, transdermal, topical, or subcutaneous administration.

As a general proposition, the therapeutically effective amount of the antimicrobial SMR peptide administered will be in the range of about 1 ng/kg body weight/day to about 100 mg/kg body weight/day whether by one or more administrations. In a particular embodiment, the range of antimicrobial SMR peptide administered is from about 1 ng/kg body weight/day to about 1 µg/kg body weight/day, I ng/kg body weight/day to about 100 ng/kg body weight/day, 1 ng/kg body weight/day to about 10 ng/kg body weight/day, 10 ng/kg body weight/day to about 1 µg/kg body weight/day, 10 ng/kg body weight/day to about 100 ng/kg body weight/day, 100 ng/kg body weight/day to about 1 µg/kg body weight/day, 100 ng/kg body weight/day to about 10 µg/kg body weight/day, 1 µg/kg body weight/day to about 10 µg/kg body weight/day, 1 µg/kg body weight/day to about 100 µg/kg body weight/day, 10 µg/kg body weight/day to about 100 µg/kg body weight/day, 10 µg/kg body weight/day to about 1 mg/kg body weight/day, 100 µg/kg body weight/day to about 10 mg/kg body weight/day, 1 mg/kg body weight/ day to about 100 mg/kg body weight/day and 10 mg/kg body weight/day to about 100 mg/kg body weight/day.

In other embodiments, the antimicrobial SMR peptide is administered at a dosage range of 1 ng-10 ng per injection, 10 ng-100 ng per injection, 100 ng-1 µg per injection, 1 µg-10 µg per injection, 10 µg-100 µg per injection, 100 µg-1 mg per injection, 1 mg-10 mg per injection, 10 mg-100 mg per injection, and 100 mg-1000 mg per injection. The antimicrobial SMR peptide may be injected daily, or every 2, 3, 4, 5, 6 and 7 days.

In other embodiments, the dose range of the antimicrobial SMR peptide administered is from about 1 ng/kg to about 100 mg/kg. In still another particular embodiment, the range of antibody administered is from about 1 ng/kg to about 10 ng/kg, about 10 ng/kg to about 100 ng/kg, about 100 ng/kg to about 1 µg/kg, about 1 µg/kg to about 10 µg/kg, about 10 µg/kg to about 100 µg/kg, about 100 µg/kg to about 1 mg/kg, about 1 mg/kg to about 10 mg/kg, about 10 mg/kg to about 100 mg/kg, about 0.5 mg/kg to about 30 mg/kg, and about 1 mg/kg to about 15 mg/kg.

In other particular embodiments, the amount of antimicrobial SMR peptide administered is, or is about, 0.0006, 0.001, 0.003, 0.006, 0.01, 0.03, 0.06, 0.1, 0.3, 0.6, 1, 3, 6, 10, 30, 60, 100, 300, 600 and 1000 mg/day.

The specific dose of antimicrobial SMR peptide is determined by the particular circumstances of the individual patient including the size, weight, age and sex of the patient, the nature and stage of the disease, the aggressiveness of the disease, and the route of administration of the antimicrobial composition.

In certain embodiments, the antimicrobial SMR peptide may be administered at least once per day, typically once, twice, three times or four times per day with the doses given at equal intervals throughout the day and night in order to maintain a constant presence of the drug in order to provide sufficient antimicrobial activity. However, a skilled artisan will appreciate that a treatment schedule can be optimized for any given patient, and that administration of compound may occur less frequently than once per day.

In other embodiments, the antimicrobial SMR peptide of the present application is prescribed to be taken in combination with other antimicrobial agents. Examples of other antimicrobial agents include, but are not limited to, antibiotics, other antimicrobial peptides, bacterial biofilm-degrading enzymes and in vivo expression vectors that encode the antimicrobial SMR peptide of the present application. When used in such combinations, the antimicrobial SMR peptide of the present application and other antimicrobial agents may be administered simultaneously, by the same or different routes, or at different times during treatment.

The treatment may be carried out for as long a period as necessary, i.e., until the infection is cleared or no longer a threat to the host. Typically it is contemplated that treatment would be continued indefinitely while the disease state persists, although discontinuation might be indicated if the antimicrobial compositions no longer produce a beneficial effect. The treating physician will know how to increase, decrease, or interrupt treatment based on patient response.

Production of the Antimicrobial SMR Peptide

The antimicrobial SMR peptide of the present application can be chemically synthesized or produced from cells transformed with polynucleotide expression vectors encoding the antimicrobial peptide using recombinant DNA technologies well known to those skilled in the art. Polynucleotide expression vectors can be designed to facilitate preparative expression levels in many different cell hosts, including bacteria, yeast, insect cells, and mammalian cells.

In some microorganisms, such as wild type *E. coli*, the periplasm constitutes an oxidizing environment, whereas the cytoplasm is a reducing environment. Accordingly, expression in the E. coli periplasm may enable the production of peptides containing interchain or intrachain disulfide bonds that might be otherwise reduced in cytoplasm, where it may be toxic to the cell. Some prokaryotic organisms have endogenous, intracellular oxidizing environments and can normally accommodate formation of protein disulfide bonds inside the cell. Accordingly, the fusion protein may be periplasmically expressed using an operably linked periplasmic signal sequence at the 5'end of the corresponding nucleic acid expression construct.

The antimicrobial SMR peptide encoded in the expression vector may further include a cleavage recognition site for proteolytic cleavage of one or more peptide domains from one another. The cleavage recognition sequence can be cleaved by a suitable protease, such as Kex2p or furin, at one or more defined residues.

Where the cleavage recognition site is positioned adjacent to an antimicrobial domain, proteolytic cleavage in a transduced cell can liberate one or more antimicrobial domains from one another so that the antimicrobial agents can function independently of one another according to their designated microbial cell surface target or microbial intracellular target.

For example, when positioned in or adjacent to an antimicrobial SMR peptide spacer region, the peptide can be directly cleaved when introduced into a microbial cell bearing the corresponding protease. In one embodiment, the proteolytic recognition site is a Kex2p-sensitive proteolytic cleavage site. In another embodiment, the proteolytic recognition site is the furin proteolytic cleavage site, which is sensitive to cleavage by the enzyme, furin.

An expression construct can further include an N-terminal signal peptide region to facilitate entry of the encoded antimicrobial SMR peptide into the secretory pathway following gene transfer into eukaryotic cells near a site of infection.

In Vivo Expression Vectors Encoding the Antimicrobial SMR Peptide

In certain embodiments, an expression vector encoding the antimicrobial SMR peptide of the present application is directly administered to a patient to express the antimicrobial SMR peptide in vivo. Suitable non-viral expression vectors include, but are not limited to, plasmid expression vectors or a bacteriophage vectors. Suitable viral vectors include, but are not limited to, retroviral vectors, lentiviral vectors, adenoviral vectors, adeno-associated viral (AAV) vectors, herpes viral vectors, and alphavirus vectors. The viral vector can also be an astrovirus, coronavirus, orthomyxovirus, papovavirus, paramyxovirus, parvovirus, picornavirus, poxvirus, togavirus viral vector.

The term "in vivo expression vector" refers to a non-viral or viral vector that comprises a polynucleotide encoding the antimicrobial SMR peptide of the present application in a form suitable for expression of the polynucleotide in a host cell. The expression vectors include one or more regulatory sequences, selected on the basis of the host cells to be used for expression, and operably linked to the polynucleotide sequence to be expressed. It will be appreciated by those skilled in the art that the design of the expression vector can depend on such factors as the choice of the host cell to be transformed, the level of expression of protein desired, and the like. The expression vectors can be introduced into host cells to thereby produce proteins or peptides, such as the antimicrobial SMR peptide of the present application.

As used herein, the term "control sequences" or "regulatory sequences" refers to DNA sequences necessary for the expression of an operably linked coding sequence in a particular host organism. The term "control/regulatory sequence" is intended to include promoters, enhancers and other expression control elements (e.g., polyadenylation signals). Control/regulatory sequences include those which direct constitutive expression of a nucleotide sequence in many types of host cells and those which direct expression of the nucleotide sequence only in certain host cells (e.g., tissue-specific regulatory sequences). An expression vector may be designed to facilitate expression of the antimicrobial SMR peptide-encoding polynucleotide in one or more cell types. Tissue-specific regulatory elements may be used to restrict expression to a particular cell type.

A nucleic acid sequence is "operably linked" to another nucleic acid sequence when the former is placed into a functional relationship with the latter. For example, a DNA for a presequence or secretory leader peptide is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

The delivery of antimicrobial SMR peptide-encoding expression vectors can be achieved by infection (for viral vectors), transfection (for non-viral vectors) and other methods well known to one skilled in the art. Examples of other delivery methods and media include, polycationic condensed DNA linked or unlinked to killed viruses, ligand linked DNA, liposomes, eukaryotic cell delivery vehicles cells, deposition of photopolymerized hydrogel materials, handheld gene transfer particle gun, ionizing radiation, nucleic charge neutralization or fusion with cell membranes. Particle mediated gene transfer may also be employed.

Plasmid DNA expression vectors can be utilized for non-viral gene transfer, either by direct injection of naked DNA or by encapsulating the antimicrobial SMR peptide-encoding polynucleotides in liposomes, microparticles, microcapsules, virus-like particles, or erythrocyte ghosts. Such compositions can be further linked by chemical conjugation to, for example, microbial translocation domains and/or targeting domains to facilitate targeted delivery and/or entry of nucleic acids into the nucleus of desired cells to promote gene expression. In addition, plasmid vectors may be incubated with synthetic gene transfer molecules such as polymeric DNA-binding cations like polylysine, protamine, and albumin, and linked to cell targeting ligands such as asialoorosomucoid, insulin, galactose, lactose or transferrin. Naked DNA may also be employed. Uptake efficiency of naked DNA may be improved using biodegradable latex beads. Such delivery may be improved further by treating the beads to increase hydrophobicity and thereby facilitate disruption of the endosome and release of the DNA into the cytoplasm.

Bacteriophage Vectors

In certain embodiments, the expression vector comprises a bacteriophage displaying the antimicrobial SMR peptide on its surface, expressing the antimicrobial SMR peptide from a bacteriophage following entry into a bacterium, or both. The bacteriophage can be specific for groups of bacteria or single strains. Bacteriophages can provide high titer incoculums and amplified spread, wherein a single particle can produce between about 10-100 particles per phage. Displaying the fusion protein on the phage surface can render the particle bactericidal, irrespective of whether the transduced cell is capable of supporting bacteriophage replication and spread.

In certain embodiments, the antimicrobial SMR peptide of the present application is recombinantly expressed from a bacteriophage in bacterial target cells permissive to bacteriophage infection. Where the cell is a permissive host for a bacteriophage genetically engineered to express the antimicrobial SMR peptide, the cell can be killed directly and program the synthesis of additional bacteriophages for amplifying the bacterial cell killing effects.

In other embodiments, the antimicrobial peptide is displayed on the bacteriophage surface as part of phage tail fiber or coat protein using phage display technologies well known to those of skill in the art. The antimicrobial peptide or bacteriophage may additionally include a targeting domain to facilitate targeted killing of a specified bacterial Gram-designation, genus, species, or strain. By way of example, a DNA encoding an antimicrobial peptide comprising one or more SMR domains, CPP domains, targeting domains, and/or other antimicrobial domains may be displayed onto a major or minor coat protein, of a filamentous bacteriophage, for example in Proteins I through VIII of phages SAP-2, M13, or T7. In addition, the bacteriophage may be modified to display a fusion protein comprising a Protein A portion or other suitable Fc-or IgG-binding region for attachment to targeting domains, including anti-microbial IgG antibodies or other antibody-based targeting agents described herein in accordance with methodologies previously described (Yacoby et al., *Antimicrob. Agents Chemother.*, 50(6):2087-2097, 2006).

Where the microbial cell is non-permissive for a bacteriophage replication, the bacteriophage can nonetheless infect and kill the cell, provided that the bacteriophage displays an antimicrobial domain and/or cell penetrating peptide domain appropriate for binding to and killing of a suitable microbial target cell.

Alternatively, antimicrobial peptides and antibiotics can be chemically conjugated onto the surface of the phage particles using chemical conjugation methodologies capable of displaying between 3,000-40,000 drug (or antibiotic) molecules per phage (see, e.g., *Antimicrob. Agents Chemother.*, 51(6): 2156-22163, 2007, and U.S. Pat. Appl. No. 2008/0057038 to Yacoby et al.).

In another embodiment, the antimicrobial SMR peptide of the present application may be displayed on a phage tail fiber or coat protein using the sortase enzyme in combination with the appropriate substrates for sortase-mediated peptide ligation (see e.g., Proft, *Biotechnol. Lett.* 32(1): 1-10 and U.S. Pat. Appl. Publ. No. 2011/0046008 to Love et al.).

Any bacteriophage may be used in the practice of the present application. In one embodiment, the bacteriophage is a lytic bacteriophage. In another embodiment, the bacteriophage is lysis-deficient. In some cases, use of lysis-deficient bacteriophages may reduce in vivo toxicity by reducing endotoxin and inflammatory mediator release. Exemplary bacteriophages for use with the antimicrobial SMR peptide of the present application include, but are not limited to, filamentous bacteriophages, *Escherichia coli* bacteriophages; Staphylococcal bacteriophages, including bacteriophage 456, P9042, a lytic phage, and P954, a lysogenic phage; bacteriophages that infect *Pseudomonal* and *Enterococcal* species, as disclosed in e.g., US Pat. Appl. Publ. No. 2011/0020290 and 2006/0140911; phage lambda, phage f1, p1 phage, phage Mu, fd, WT phage, M13, φX174, φ6, φ20, φ29, φGH4, φDGH4, φDGH6, φDGH13, φDGH14, R17, T12, T7, T4, T2, A511, L5, P58, KS, K1, PM2, P22, K1-5, ENB6, IRA, SP6, twort phage, RZh, H4489a, A511:: luxAB, and phAE40.

Articles and Methods for Biofilm Prevention and Dispersal

The inventors of the present application have unexpectedly discovered that the HIV-1 Nef SMR peptide sequesters Mortalin, a heat shock and chaperone protein involved in vesicle trafficking, as well as its bacterial chaperone homolog (DnaK), also known as heat shock protein 70 (Hsp70). DnaK is known to play important roles in protein folding and refolding of denatured and aggregated proteins and contributes to diverse cellular functions, including stress responses, cell division, motility, and pathogenesis. A number of investigators have suggested that Dnak plays a role in biofilm formation (Singh et al., 2012. *Int. J. Med. Microbiol.*, 302:242-252; Lemos et al., 2007. *J. Bacteriol.* 189: 1582-1588; Arita-Morioka et al., 2015. *Antimicrob. Agents Chemother.*, 59(1):633-641.

Consistent with the interaction between SMR peptide and Dnak (see FIG. 8), the HIV-1 Nef SMR peptide has been shown to prevent or reduce biofilm formation and/or dispersal of bacteria from formed biofilms (see Example 5, FIGS. 12-16).

Biofilms are complex communities of microorganisms that attach to surfaces and are embedded in a self-produced extracellular matrix. Since these cells acquire increased tolerance against antimicrobial agents and host immune systems, biofilm-associated infectious diseases tend to become chronic. Biofilms have been found to be involved in a wide variety of microbial infections in the body, by one estimate 80% of all infections. Infectious processes in which biofilms have been implicated include common problems such as bacterial vaginosis, urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses, heart valves, and intervertebral disc.

Indeed, a principal concern with respect introducing medical products into the body (e.g., contact lenses, central venous catheters, mechanical heart valves and pacemakers) is their susceptibility to microbial infection and invariably biofilm formation. As these infections are difficult to treat with antibiotics, removal of the device is often necessitated, which is traumatic to the patient and increases medical costs.

In view of the foregoing, the antimicrobial peptides of the present invention have many applications.

In one embodiment, a method for treating a microbial infection comprises administering to a subject in need thereof, a composition comprising an antimicrobial SMR peptide of the present application. In preferred embodiment, this method is used for treating difficult-to-treat antibiotic-resistant and/or nosocomial (e.g., hospital-acquired) infection in patients caused by microbial biofilms in vivo.

Antibiotic-resistant and/or nosocomial infections are caused by microbes including, but not limited to, antibiotic resistant strains, such as fluoroquinolone-resistant *Pseudomonas aeruginosa* (FQRP), *Acinetobacter* species and Enterobacteriaceae such as *E. coli, Salmonella, Shigella, Citrobacter, Edwardsiella, Enterobacter, Hafnia, Klebsiella, Morganella, Proteus. Providencia, Serratia* and *Yersinia* species; methicillin-resistant *Staphylococcus aureus* (MRSA), vancomycin-resistant *Enterococcus* (VRE) species, including *E. faecalis* and *E. faecium; Streptococcus pneumoniae, Propionibacterium acnes*, multidrug-resistant *Mycobacterium tuberculosis*.

In another embodiment, a method for dispersing a biofilm or detaching a biofilm from a surface comprises contacting a biofilm or surface with a composition comprising an antimicrobial SMR peptide of the present application. This method can be adapted to disperse or detach a biofilm in a variety of unrelated industries, including the food, agriculture, pharmaceutical, paint, water, shipping and engineering industries. Thus, the method can be applied to prevention or removal of contaminations in health care, agriculture, and industrial settings, in particular in water pipes of hospitals, in water, plumbing, ventilation, building heating, air conditioning, oil wells, cosmetics and medicaments.

In some embodiments, the antimicrobial SMR peptide of the present application are used for treating surfaces of medical devices, natural or synthetic implants, prosthetics, surgical instruments and implements, dental products, and the like. As used herein, unless otherwise noted, the term "surface" is used interchangeably with the term "solid support." As such, the antimicrobial SMR compositions may be used to coat the inner and outer aspects of various instruments and devices, whether disposable or intended for repeated uses. Such surfaces can include a broad spectrum of articles adapted for medical use, including without limitation, scalpels, needles, scissors and other devices used in invasive surgical, therapeutic or diagnostic procedures; blood filters, and the like.

By coating surfaces of medical devices, implants and the like, the SMR peptide compositions of the present application can prevent adherence of microorganisms thereto so as to reduce/eliminate any possible cell aggregation and biofilm formation known to occur following implantation. Device-related infections usually result from the introduction of microorganisms, primarily bacteria, during the device insertion or implantation procedure, or from attachment of blood-borne organisms to the newly inserted device and their subsequent propagation on its surface. Coating the medical device with the compositions of the present application can therefore inhibit biofilm formation of one or more microbial species, prevent medical device related infections, and consequently can reduce the need of antibiotic treatment or removal of the medical device from the subject.

Exemplary medical devices, instruments, and implants whose surfaces are susceptible to biofilm formation include, but are not limited to, any object that is capable of being implanted temporarily or permanently into a mammalian organism, such as a human. Representative medical devices, instruments, and implants that may be used according to the present application include, for example, central venous catheters, urinary catheters, endotracheal tubes, mechanical heart valves, pacemakers, vascular grafts, stents and prosthetic joints. Medical devices that may be coated according to the teachings of the present application may further include artificial blood vessels, catheters and other devices for the removal or delivery of fluids to patients, artificial hearts, artificial kidneys, orthopedic pins, prosthetic joints, plates and implants; catheters and other tubes (including urological and biliary tubes, endotracheal tubes, intubation tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, mechanical heart valves, artificial joints, artificial larynxes, otological implants), intrauterine devices, anastomotic devices, vascular catheter ports, vascular stents, clamps, embolic devices, wound drain tubes, ocular lenses, dental implants, dentures, dental crowns, dental caps, hydrocephalus shunts, pacemakers and implantable defibrillators, needleless connectors, voice prostheses and the like.

In other embodiments, the antimicrobial compositions, including the SMR peptides, can be included in a dental preparation to provide an antimicrobial effect to the mouth, teeth and gums and for treatment of dental and gum diseases. Preferably, the dental preparation is selected from the group comprising a gel, spray, mouthwash, toothpaste, lozenge or chewing gum. In particular embodiments, a dental preparation containing the SMR peptides of the present application are particularly useful in reducing the number of *Streptococcus mutans*, which are an important cause of dental caries. In other embodiments, the antimicrobial SMR peptides may be used to provide an antimicrobial effect to the mouth, teeth and gums, such as by incorporation in a toothpaste, mouthwash, or chewing gum.

Surfaces found in the medical environment also include the inner and outer aspects of pieces of medical equipment, medical gear worn or carried by personnel in the health care setting. Such surfaces can include surfaces intended as biological barriers to infectious organisms in medical settings, such as gloves, aprons and face shields. Commonly used materials for biological barriers are thermoplastic or polymeric materials such as polyethylene, dacron, nylon, polyesters, polytetrafluoroethylene, polyurethane, latex, silicone and vinyl. Other surfaces can include counter tops and fixtures in areas used for medical procedures or for preparing medical apparatus, tubes and canisters used in respiratory treatments, including the administration of oxygen, of solubilized drugs in nebulizers and of anesthetic agents. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered. The antimicrobial compositions of the present application can be used on the surface of or within these medical devices to provide long term protection against colonization by single cell organisms and reduce the incidence of device-related infections. In certain embodiments, the peptides are covalently attached to the medical device polymer. Alternatively, the SMR peptides or other active agents of the present application can be directly incorporated into the polymeric matrix of the medical device at the polymer synthesis stage or at the device manufacture stage.

The antimicrobial SMR peptides and other active agents of the present application can be attached directly or indirectly (i.e., by a linking group) to surfaces or solid supports by any means known in the art. Preferably, the antimicrobial peptides and/or other active agents are directly attached to the solid support by covalent attachment. Alternatively, the antimicrobial peptides and/or other active agents may be modified to permit covalent attachment to a solid support or surface. Exemplary surfaces for attachment include any surface to which a single cell microorganism can attach, including fabrics, fibers, foams, films, concretes, masonries, glass, metals, plastics, polymers, and like.

The surface is not limited and includes any surface on which a microorganism may occur, particularly, as noted above, a surface exposed to water or moisture. The surface may be biotic or abiotic, and inanimate (or abiotic) surfaces include any such surface which may be exposed to microbial contact or contamination. Thus, surfaces for treatment may include surfaces on machinery, notably industrial machinery, or any surface exposed to an aquatic environment (e.g., marine equipment, or ships or boats or their parts or components), or any surface exposed to any part of the environment e.g., pipes or on buildings. Such inanimate surfaces exposed to microbial contact or contamination include in particular any part of: food or drink processing, preparation, storage or dispensing machinery or equipment, air conditioning apparatus, industrial machinery e.g., in chemical or biotechnological processing plants, storage tanks and medical or surgical equipment.

Any apparatus or equipment for carrying or transporting or delivering materials, which may be exposed to water or moisture is susceptible to biofilm formation. Such surfaces may include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

Underwater surfaces include any water immersed surface, including hulls of a ship or boat (i.e., the body or frame of a ship or boat), submergence vehicles, navigational aids, screens, nets, constructions, floating or emplaced offshore platforms (e.g., docks), buoys, signaling equipment and articles which come into contact with sea water or salty water. Other underwater surfaces include structures exposed to sea water including pilings, marine markers, undersea conveyances like cabling and pipes, fishing nets, bulkheads, cooling towers, and any device or structure that operates submerged.

The antimicrobial SMR peptide of the present application can be incorporated into marine coatings to limit undesirable marine biofouling. In a particular embodiment, the antimicrobial peptides for use in biofouling application can be formulated in an anti-biofouling paint so as not to contain toxic materials (such as heavy metals), yet still retain their efficacy as biofouling agents.

An anti-biofouling paint of the present application may further contain binders(s), pigment(s), solvent(s) and additive(s). Exemplary solvents include aromatic hydrocarbons such as xylene and toluene; aliphatic hydrocarbons such as hexane and heptane, esters such as ethyl acetate and butyl acetate; amides such as N-methylpyrrolidone and N,N-dimethylformamide; alcohols such as isopropyl alcohol and butyl alcohol; ethers such as dioxane, THF and diethyl ether; and ketones such as methyl ethyl ketone, methyl isobutyl ketone and methyl isoamyl ketone. The solvents may be used alone or in combination thereof.

Exemplary binders include alkyd resin, acrylic or vinyl emulsions, polyurethane resins, epoxy resins, silicone based resins, acrylic resins, inorganic silicate based resins, vinyl resins, particularly a vinyl chloride/vinyl acetate copolymer, and rosin. Exemplary pigments include titanium dioxide, cuprous oxide, iron oxide, talc, aluminum flakes, mica flakes, ferric oxide, cuprous thiocyanate, zinc oxide, cupric acetate meta-arsenate, zinc chromate, zinc dimethyl dithiocarbamate, zinc ethylene bis(dithiocarbamate) and zinc diethyl dithiocarbamate.

Exemplary additives include dehumidifiers, wetting/dispersing agents, anti-settling agents, anti-skinning agents, drying/curing agents, anti-marring agents and additives ordinarily employed in coating compositions as stabilizers and anti-foaming agents. Additionally, any antibiotic which is relatively insoluble in seawater can be used with an anti-biofouling marine paint.

Exemplary devices or equipment whose surfaces are susceptible to biofilm formation include, but are not limited to, vessel hulls, automobile surfaces, airplane surfaces, membranes, filters, and industrial equipment. The surface may also be present in medical devices, instruments, and implants.

Additional surfaces that can be treated according to the teachings of the present application include the inner and outer aspects of those articles involved in water purification, water storage and water delivery, and those articles involved in food processing. Thus the present application envisions coating a solid surface of a food or beverage container to extend the shelf life of its contents.

Surfaces related to health can also include the inner and outer aspects of those household articles involved in providing for nutrition, sanitation, disinfection or disease prevention. Thus, the antimicrobial compositions of the present application can be used for prevention or removal of disease-causing microorganisms from external surfaces. As such, the antimicrobial SMR peptides may be used for eliminating, reducing or preventing bacterial biofilms as a disinfectant e.g., in hospital, dental surgery, veterinary, kitchen or bathroom, whereby the antimicrobial SMR peptides are prepared in a composition in form of e.g., a fluid, a powder, a gel, or an ingredient of a wet wipe or a disinfection sheet product. Additional applications include, for example, treatment of food processing equipment for home use, treatment of materials for infant care, tampons, soap, detergents, health and skincare products, household cleaners, and toilet bowls.

Compositions comprising the antimicrobial SMR peptides may additionally comprise suitable carriers, additives, diluting agents and/or excipients for its respective use and form, respectively,—but also with agents that support the antimicrobial activity, such as EDTA and other agents enhancing the antimicrobial- and anti-biofilm activity of the antimicrobial SMR peptides.

For example, the antimicrobial SMR peptides may be used with common disinfectant agents like, alcohols, aldehydes, oxidizing agents, phenolics, quaternary ammonium compounds or UV-light. For disinfecting surfaces, objects and/or devices, the peptides can be applied on the surfaces, objects and/or devices. The application may occur, for example, by wetting the disinfecting composition with any means such as a cloth or rag, by spraying, pouring.

In some embodiments, the compositions are used for impregnating or coating or covering items, including but not limited to surgical gloves, catheters, artificial joints, breast implants, heart valves, pacemakers etc.

Biofilms play a central role in the pathogenesis of serious-infections caused by *Staphylococcus aureus* and coagulase negative *staphylococci* (CONS), often implicated in chronic wound infections and medical device-related infections.

In some embodiments, the peptides may be included in a wound dressing or matrix. A wound dressing comprising the antimicrobial compositions of the present application may be used to treat an acute wound or a chronic wound. Acute wounds are wounds that proceed orderly through the three recognized stages of the healing process (i.e. the inflammatory stage, the proliferative stage and the remodeling phase) without a protracted time course. Chronic wounds, however, are those wounds that do not complete the ordered sequence of biochemical events because the wound has stalled in one of the healing stages. Viewed alternatively a chronic wound is a wound that has not healed within at least 40 days, preferably at least 50 days, more preferably at least 60 days, most preferably at least 70 days. Chronic wounds are a major health problem throughout the world and represent a significant drain on clinical resources.

Wounds are an ideal environment for the formation of biofilms due to their susceptibility to contamination and the availability of substrate and surface for biofilm attachment. The wound to be treated may be a breach in, or denudement of, the tissue for instance caused by surgical incision or trauma, e.g., mechanical, thermal, electrical, chemical or radiation trauma; a spontaneously forming lesion such as a skin ulcer (e.g. a venous, diabetic or pressure ulcer); a blister (e.g. a friction or thermal blister or a blister caused by pathogen infection such as chicken pox); an anal fissure or a mouth ulcer. Body or tissue surfaces which are dead or damaged (e.g. necrotic or inflamed) are particularly susceptible to biofilm infection. Chronic wound infections share two important attributes with other biofilm infections: persistent infection that is not cleared by the host immune system even in individuals with healthy innate and adaptive immune reactions, and resistance to systemic and topical antimicrobial agents. Accordingly, biofilm based infection are difficult to treat and biofilm contamination is difficult to eradicate using conventional antibiotics.

The presence of biofilms may be determined by various tests, including the Tissue culture plate method (TCP) (Christensen et al., *J Clin Microbiol* 22:996-1006 (1985)); the Tube method (TM) (Christensen et al., *Infect Inmun* 37:318-26 (1982)), and the Congo red Agar method (CRA) (Freeman et al., *J Clin Pathol* 42:872-4 (1989)). The biofilm may be quantified by using a crystal violet assay (Peeters et al., *J Microbiol Methods* 72: 157-165 (2008)).

In certain embodiments, the antimicrobial compositions of the present application are used to coat or cover or at least provide an overlayer for plastic items (e.g., polyethylene etc.) and metal surfaces susceptible to bacterial infections, including biofilm formation.

Biofilms are also known to cause accelerated corrosion in industrial systems, oil souring and biofouling. Biofouling may be caused by the adhesion of organisms to any surface in a marine or freshwater environment, including cooling towers, water pipes and filters in cooling or desalinization installations, irrigation and power stations, and membranes, such as those used in wastewater and desalinization systems. Biofouling also occurs in aquaculture systems in fish farms. Furthermore, commercial shipping fleets of the world consume approximately 300 million tons of fuel annually. Without antifouling measures, fuel consumption would increase by as much as 40%. The economic cost of such antifouling measures has been estimated to be about $30 billion annually. Generally, biofilms are very difficult to eliminate, since microbes growing within are highly organized and can withstand hostile environments, such as high temperatures and anti-microbial agents (e.g., antibiotics).

In one embodiment, the present application provides a method of dispersing a biofilm or detaching biofilm formation from a surface, the method comprising treating water with or coating the surface with a composition comprising an antimicrobial SMR peptide according to the present application, wherein the composition is capable of detaching a single cell organism from a surface or from other single cell organisms.

A composition containing the antimicrobial SMR peptides of the present application may be formulated to protect the active peptides from environmental influences such as proteases, oxidation, immune responses etc., until they reach the site of infection. Therefore, the formulation may be in the form of a capsule, dragee, pill, powder, suppository, emulsion, suspension, gel, lotion, cream, salve, injectable solution, syrup, spray, inhalant or any other medical reasonable galenic formulation. Preferably, the galenic formulation may comprise suitable carriers, stabilizers, flavorings, buffers or other suitable reagents.

For example, for topical application the formulation may be a lotion, cream, gel, salve or plaster; for nasopharyngeal application the formulation may be saline solution to be applied via a spray to the nose. For oral administration, it may be necessary to protect the peptides from the harsh digestive environment of the stomach before reaching the site of the infection. Therefore, in certain embodiments, the peptides may be covered by a polysaccharide coating that is resistant to erosion in both the stomach and intestine. Such polymers can be only degraded in the colon, which contains a large microflora containing biodegradable enzymes breaking down, for example, the polysaccharide coatings to release the peptide and/or drug within. Exemplary polysaccharide coatings may include, for example, amylose, arabinogalactan, chitosan, chondroitin sulfate, cyclodextrin, dextran, guar gum, pectin, xylan, and combinations or derivatives therefrom.

Combination Therapies and Treatments

In order to enhance the antimicrobial properties of the SMR peptides, improved treatment efficacy, and/or facilitate targeting of multiple steps involved in microbial biofilm development, the antimicrobial SMR peptides may be combined with other anti-biofilm peptides (e.g., AMPs), antibiotics, matrix-inhibiting compounds, matrix-disaggregating compounds, and quorum sensing inhibitors. This combination treatment can reduce the effective concentration of each antimicrobial agent required for treatment, as well as the cost of effective treatment. Such combination treatments can be further used for treatment of surfaces or any of the other applications described herein.

In one embodiment, the antimicrobial SMR peptide of the present application is further modified to include a second antimicrobial domain comprising a known AMP sequence. Alternatively, the antimicrobial SMR peptide can be included in a composition along with one or more other AMPs. The inclusion of other AMPs or bacteriocins enhances the antimicrobial activity of the antimicrobial SMR peptide of the present application and/or facilitates the uptake of the antimicrobial peptide by the microorganism. Exemplary AMPs include, but are not limited to, andropin, apidaecin, bacteriocin leucocin A, bactenecin, bactenecin-7, buforin II, cathelicidin LL-37, clavanin A, cecropin, cecropin A-magainin 2 hybrid peptide, dermcidin-IL, cyclic dodecapeptide, β-defensin I, α-defensin (HNP-1), E3-APO, gaegurin, histatin, histatin-5, indolicidin, magainin 2, melittin B, nisin A, novispirin G10, pyrrhocoricin, protegrin, protegrin PG-1, ranalexin, tachyplesin-1, and tachyplesin-1 analog. In certain embodiments, the AMP or bacteriocin is capable of degrading a bacterial cell wall, such as lyostaphin (degrading *Staphylococcus* cell walls), mutanolysin (degrading *Streptococcus* cell walls) and enterolysin (degrading *Enterococcus* cell walls). It is noted that to the extent that a composition comprises an AMP in addition to the SMR peptide of the present application, the AMP may be produced and/or modified according to any the disclosed methods and compositions pertaining to the SMR peptide.

In another embodiment, the antimicrobial SMR peptide of the present application is combined with a conventional antibiotic. In preferred embodiments, the SMR peptide acts synergistically with a conventional antibiotic to reduce the effective amount(s) or SMR peptide or antibiotics needed for anti-microbial and/or anti-biofilm activity. The conventional antibiotics include anti-bacterial and anti-fungal antibiotics.

There are several generally recognized categories of bacterial antibiotic agents including (1) penicillins, (2) cephalosporins, (3) quinolones, (4) aminoglycosides, (5) monobactams, (6) carbapenems, and (7) macrolides. Specific examples of bacterial antibiotics for use with the SMR peptides of the present application include, but are not limited to, afenide, amikacin, amoxicillin, ampicillin, arsphenamine, augmentin, azithromycin, azlocillin, aztreonam, bacampicillin, bacitracin, balofloxacin, besifloxacin, capreomycin, carbacephem (loracarbef), carbenicillin, cefacetrile (cephacetrile), cefaclomezine, cefaclor, cefadroxil (cefadroxyl), cefalexin (cephalexin), cefaloglycin (cephaloglycin), cefalonium (cephalonium), cefaloram, cefaloridine (cephaloradine), cefalotin (cephalothin), cefamandole, cefaparole, cefapirin (cephapirin), cefatrizine, cefazaflur, cefazedone, cefazolin (cephazolin), cefcanel, cefcapene, cefclidine, cefdaloxime, cefdinir, cefditoren, cefedrolor, cefempidone, cefepime, cefetamet, cefetrizole, cefivitril, cefixime, cefluprenam, cefmatilen, cefmenoxime, cefmepidium, cefmetazole, cefodizime, cefonicid, cefoperazone, cefoselis, cefotaxime, cefotetan, cefovecin, cefoxazole, cefoxitin, cefozopran, cefpimizole, cefpirome, cefpodoxime, cefprozil (cefproxil), cefquinome, cefradine (cephradine), cefrotil, cefroxadine, cefsumide, ceftaroline, ceftazidime, ceftazidime/avibactam, cefteram, ceftezole, ceftibuten, ceftiofur, ceftiolene, ceftioxide, ceftizoxime, ceftobiprole, ceftriaxone, cefuracetime, cefuroxime, cefuzonam, cephalexin, cephalothin, chloramphenicol, chlorhexidine, ciprofloxacin, clarithromycin, clavulanic acid, clinafloxacin, clindamycin, cloxacillin, colimycin, colistimethate, colistin, crysticillin, cycloserine, daptomycin, demeclocycline, dicloxacillin, dirithromycin, doripenem, doxycycline, efprozil, enoxacin, ertapenem, erythromycin, ethambutol, flucloxacillin, flumequine, fluoroquinolones, fosfomycin, furazolidone, fusidic acid, gatifloxacin, geldanamycin, gemifloxacin, gentamicin, glycopeptides, grepafloxacin, herbimycin, imipenem, isoniazid, kanamycin, levofloxacin, lincomycin, linezolid, lipoglycopeptides, lomefloxacin, meropenem, meticillin, metronidazole, mezlocillin, minocycline, mitomycin, moxifloxacin, mupirocin, nadifloxacin, nafcillin, nalidixic acid, neomycin, netilmicin, nitrofurantoin, norfloxacin, novobiocin, ofloxacin, oxacillin, oxazolidinones, oxolinic acid, oxytetracycline, oxytetracycline, paromomycin, pazufloxacin, pefloxacin, penicillin G, penicillin V, pipemidic acid, piperacillin, piromidic acid, pivampicillin, pivmecillinam, platensimycin, pleuromutilins, polymyxins (e.g., polymyxin B), pristinamycin, prontosil, prulifloxacin, pvampicillin, pyrazinamide, quinupristin/dalfopristin, retapamulin, rifabutin, rifalazil, rifampicin/rifampin, rifamycin, rifapentine, rosoxacin, roxithromycin, rufloxacin, sitafloxacin, sparfloxacin, spectinomycin, spiramycin, streptomycin, sulbactam, sulfacetamide, sulfamethizole, sulfamethoxazole, sulfanilimide, sulfisoxazole, sulfonamides, sultamicillin, teicoplanin, telavancin, telithromycin, temafloxacin, tetracyclines, thiamphenicol, ticarcillin, tigecycline, tinidazole, tobramycin, tosufloxacin, trimethoprim, trimethoprim-sulfamethoxazole, troleandomycin, trovafloxacin, tuberactinomycin, vancomycin, viomycin, pharmaceutically acceptable salts thereof, and structural analogs thereof.

Exemplary anti-fungal agents include, but are not limited to, abafungin, albaconazole, amorolfin, amphotericin B, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, pharmaceutically acceptable salts thereof, and structural analogs thereof.

In another embodiment, the antimicrobial SMR peptide of the present application is combined with matrix-inhibiting agent. As used herein, the term "matrix-inhibiting agent" refers to a substance capable of inhibiting the synthesis of extracellular polymeric substances (EPS). EPS components, such as exopolysaccharides, exoproteins, and extracellular DNA (eDNA), mediate cell-to-cell and cell-to-surface connections, play a crucial role in biofilm formation and stabilization and create a physical barrier that protects biofilm cells against host immune system and antimicrobial agents (Grassi et al., *Front. Microbiol.*, 8:2409 (Dec. 2017). Matrix-inhibiting compounds for use with the SMR peptides of the present application include sulfhydryl compounds and iron chelators. Exemplary sulfhydryl compounds include, but are not limited to, dithiothreitol (DTT), β-mercaptoethanol, and L-cysteine. Exemplary iron chelators include, but are not limited to 2,2'-dipyridyl (2DP), deferoxamine mesylate (DM), 2,3-dihydroxybenzoic acid (DHBA), 2,3 dihydroxybenzaldehyde, diethylenetriaminepentaacetic acid (DTPA), ethylenediaminetetraacetic acid (EDTA), ethylenediamine-N,N'-diacetic acid (EDDA), lactoferrin, ovotransferrin, and serrotransferrin.

In another embodiment, the antimicrobial SMR peptide of the present application is combined with a matrix-disaggregating agent. As used herein, the term "matrix-disaggregating agent" refers to a substance capable of disassembling an extracellular matrix. Matrix-disaggregating agents for use with the SMR peptides include matrix-degrading enzymes, such as deoxyribonucleases (e.g., DNAse I, thermonuclease); glycoside hydrolases (e.g., dispersin B and alginate lyase); chelating agents (e.g., EDTA, EGTA, and DTPA); the fatty acid cis-2-decanoic acid; and nitric oxide producing agents (e.g., NO donor compounds, such as diazeniumdiolates, S-nitrosothiols, sodium nitroprusside (SNP) etc.), NO-releasing methodologies reducing of nitrite substrates using a copper(II)-tri(2-pyridylmethyl)amine (Cu(II)TPMA) complex as a mediator as described in e.g., U.S. Pat. Nos. 8,034,384, 8,697,771, and 9,480,785, or using diazeniumdiolate-functionalized polysiloxane macromolecules as described in U.S. 2012/0134951).

Inasmuch as endogenous proteases are known to play a role in biofilm dispersal and exogenously added proteases have been shown exhibit dispersal activity against established biofilms, proteases may be included with the SMR peptides of the present application to modulate and degrade the protein component of the biofilm matrix, provided that their specificity does not target the SMR peptide or other peptide components within the antimicrobial composition. Exemplary proteases contemplated for use with the SMR peptides of the present application include, for example, the serine protease Esp, which is produced by *S. epidermidis*;

the elastase LasB, which is produced by *P. aeruginosa*, the metalloprotease serratopeptidase (SPEP); and proteinase K.

In another embodiment, the antimicrobial SMR peptide of the present application is combined with a quorum sensing inhibitor (QSI). Quorum sensing (QS) involves the production, release, and population-wide detection of extracellular signal molecules or autoinducers. A variety of organic molecules have been associated with QS, including AHLs in Gram-negative bacteria, oligopeptides in Gram-positive bacteria, and autoinducer-2 (AI-2) acting as universal interspecies signal. QS molecules induce group-based behaviors in bacterial population, among which are virulence factor production and biofilm formation. QS allows bacteria to collectively carry out tasks that would be unsuccessful if carried out by an individual bacterium acting alone and is essential to the formation or dispersal of biofilms. QS can be reduced to interplay between two proteins; the first produces a signaling molecule known as an autoinducer (AI), and a second protein that responds to the AI. Autoinducers encompass several classes of structurally related molecules including acyl homoserine lactones (AHLs), autoinducing peptides (AIPs) and autoinducer-2 (AI-2).

As used herein, the term "quorum sensing inhibitor" (QSI) refers to a compound or substance that interferes with bacterial communication by inhibiting AHL expression, dissemination, and/or signal generation; by degrading signaling molecules; and/or impeding signal reception. Exemplary QSIs include, but are not limited to, 4-nitropyridine-N-oxide, brominated furanones, furanone C-30, (5Z)-4-bromo-5-(bromomethylene)-3-butyl-2(5H)-furanone, RNA III inhibiting peptide (RIP), S-allyl cysteine, garlic extract, p-benzoquinone, DHP (S-methylene-1-(prop-2-enoyl)-4-(2-fluorophenyl)-dihydropyrrol-2-one), thiazolidinedione-8 (TZD-8), 2,4,5-tri-bromo-imidazole, 3-amino-benzen-sulfonamide, and 3-nitro-benzen-sulfonamide; AHL analogs that compete and/or interfere with AHL binding to a receptor (e.g., LuxR); *Bacillus* AiiA enzyme, known to hydrolyzes AHLs; antagonist AHLs, such as AHLs with a longer acyl side chains (e.g., extended with at least one methylene); AHLs with decreased acyl side chain rotation (e.g., introduction of an unsaturated bond close to the amide linkage) or a substitution to the phenyl ring (e.g., para-bromo); AIP-I and TrAIP-II peptides; SsoPox enzyme from *Sulfolobus solfataricus*, and the LasR-, RhIR- and PqsR inhibitors described in U.S. 2017/0231962.

An antimicrobial composition comprising an SMR peptide of the present application may include any one or a combination of the above-described secondary products. The secondary products may be additionally included in the composition or they may be conjugated to covalently linked to the SMR peptides. Thus, for example, where the secondary agent is a peptide or enzyme, it may be synthetically fused to the SMR peptide or it may be fused via a linker to the peptide by genetic engineering according to the disclosure herein.

Pharmaceutical Compositions

The present application further provides a pharmaceutical composition comprising (1) an antimicrobial SMR peptide of the present application, an in vivo expression vector encoding the antimicrobial SMR peptide of the present application, or both, and (2) a pharmaceutically acceptable carrier. In certain embodiments, the pharmaceutical composition further comprises one or more antimicrobial peptides (e.g., AMPs), antibiotics, matrix-inhibiting compounds, matrix-disaggregating compounds, and/or quorum sensing inhibitors.

As used herein the language "pharmaceutically acceptable carrier" is intended to include any and all solvents, solubilizers, fillers, stabilizers, binders, absorbents, bases, buffering agents, lubricants, controlled release, vehicles, diluents, emulsifying agents, humectants, lubricants, dispersion media, coatings, antibacterial or antifungal agents, isotonic and absorption delaying agents, and the like, compatible with pharmaceutical administration. The use of such media and agents for pharmaceutically active substances is well-known in the art. See e.g., A. H. Kibbe Handbook of Pharmaceutical Excipients, 3rd ed. Pharmaceutical Press, London, UK (2000). Except insofar as any conventional media or agent is incompatible with the active compound, use thereof in the compositions is contemplated. Supplementary agents can also be incorporated into the compositions. In certain embodiments, the pharmaceutically acceptable carrier comprises serum albumin.

The pharmaceutical composition of the application is formulated to be compatible with its intended route of administration. Examples of routes of administration include parenteral, e.g., intrathecal, intra-arterial, intravenous, intradermal, subcutaneous, oral, transdermal (topical) and transmucosal administration.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene, glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an antimicrobial peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Stertes; a glidant such as colloidal silicon dioxide, a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or controlled release of the active ingredient. Biodegradable, biocompatible polymers can be used, such as ethylene vinyl acetate, polyanhydrides, polyglycolic acid, collagen, polyorthoesters, and poly lactic acid. Methods for preparation of such formulations will be apparent to those skilled in the art. The materials can also be obtained commercially from e.g., Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Suitable unit dosage forms include, but are not limited to powders, tablets, pills, capsules, lozenges, suppositories, patches, nasal sprays, injectibles, implantable sustained-release formulations, lipid complexes, etc.

Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the present application are dictated by and directly dependent on the unique characteristics of the active compound and the particular therapeutic effect to be achieved, and the limitations inherent in the art of compounding such an active compound for the treatment of individuals.

Toxicity and therapeutic efficacy of the antimicrobial SMR peptide and/or AMPs of the present application can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present application, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The present application is further illustrated by the following examples that should not be construed as limiting. The contents of all references, patents, and published patent applications cited throughout this application, as well as the Figures and Tables, are incorporated herein by reference.

Examples

Example 1: The HIV-1 Nef SMR Wt Peptide Disrupts Secretion Activity of Mortalin (DnaK Homologue)

Drug resistance can be caused by: 1) production of enzymes that inactive or destroy the antimicrobial drug; 2) modification of the drug's target site; 3) expression efflux systems that pump out the drug before it can reach its intracellular target; or 4) the production of alternative metabolic pathway that bypasses the action of the drug. Resistance genes coding for proteins that perform these functions may be exchanged within and between bacterial species. Horizontal transfer of resistance genes occurs through transformation, transduction or conjugation. Resistance genes can be found on plasmids, transposons and integrons, unique genetic elements able to capture, integrate and express gene cassettes encoding resistance. Cell to cell transfer of resistance genes is often facilitated by a multi-component device known as a type IV secretion system, which acts to transport antibiotic resistance genes from within one cell, through its membrane and into a neighboring cell.

Translocation of the drug-resistant gene product crosses the inner membrane, requires chaperones for transit and folding of those proteins. The chaperone protein DnaK has been shown to be a central factor in a multiprotein bacterial chaperone system that includes a variety of co-chaperone proteins such as DnaJ and GrpE. This general chaperone system is in concert with either the SecB chaperone using the Sec secretion machinery, or the second, Twin-arginine Translocation (Tat) secretion pathway. DnaK is also involved in the replication of the bacterial chromosome, and plasmids. Bacteria with mutations in the DnaK/DnaJ molecules have been found to have lower growth rates, greater susceptibility to environmental stress, reduced viability in cellular environments, reduced ability to establish infections in vivo, and they are more susceptible to antibiotics compared to the wild-type strains. Thus, molecules targeting Dnak could disrupt bacterial growth, viability, and antibiotic drug resistance and constitute a new class of antimicrobial or antibacterial therapeutic.

Figure 2:
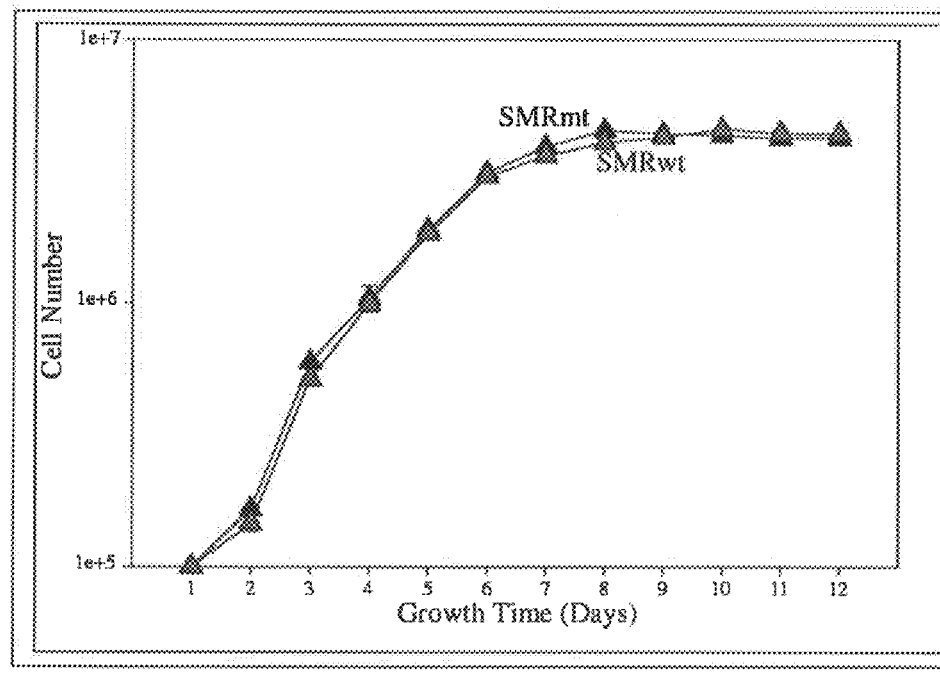
FIG. 2 is a diagram showing that the antimicrobial peptide has no effect on eukaryotic cell growth. Jurkat cultures seeded at low density were grown in the presence of the SMRwt or the SMRmut peptide. A small but consistent aliquot was taken from each culture daily over a period of 12 days. The cells in the aliquot were counted and the cells/ml in the culture calculated to determine culture growth. The data are shown with time on the x-axis and cell number on the y-axis.
Figure 3:
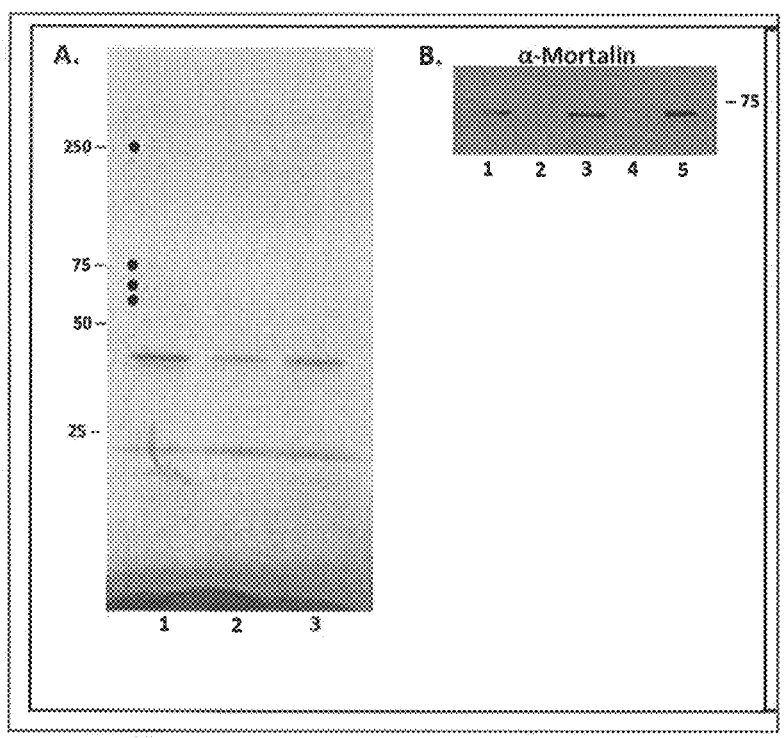
FIG. 3 is a composite of pictures showing that mortalin is a Nef SMR-specific protein. Panel A: The SMRwt peptide (lane 1) was used to immunoprecipitate Jurkat cell proteins with molecular weights of 60, 65, 75 and 250 kDa (black circles) that were visible be Coomassie staining, and which were not pulled down in its absence (lane 2), or with the SMRmut peptide (Lane 3). Panel B; An α-mortalin antibody reacted with an about 75 kDa protein in the Jurkat cell lysate (lane 1), the SMRwt peptide eluate (Lane 3), and the post-elution SMRwt peptide affinity resin (Lane 5), but failed to react with any proteins pulled down with the SMRmut peptide (Lane 4), or in the absence of either peptide (Lane 2).

FIG. 1 shows the sequence of an HIV-1 Nef SMRwt peptide having the sequence of VGFPVAAVGFPVDYKDDDDK (SEQ ID NO: 5), which is the peptide of SEQ ID NO: 3 with a Flag peptide epitope (i.e., DYKDDDDK, SEQ ID NO: 6) at the C-terminal end, and HIV-I Nef SMRmut peptide (i.e., AGFPVAAAGFPVDYKDDDDK, SEQ ID NO:7, negative control), as well as the vector constructs expressing either HIV-I Nef SMRwt peptide fused with GFP, or HIV-1 Nef SMRmut peptide fused with GFP (panel B). As shown in FIG. 2, the SMRwt and SMRmut peptides have no effect on eukaryotic cell growth. Neither peptide cause cell death (data not shown). Using immunoprecipitation with the SMRwt peptide as bait to screen for cellular factors interacting with the SMR domain, a cellular protein Mortalin was co-immunoprecipitated with the SMRwt peptide (FIG. 3). Mortalin, also known as Glucose-regulated protein 75 (GRP75) and Peptide-binding protein 74, is a 679 amino acid long, uninducible member of the heat shock protein 70 family. It has a high degree of identity with other members of the Hsp70 family, including *Escherichia coli* DnaK.

Figure 4:
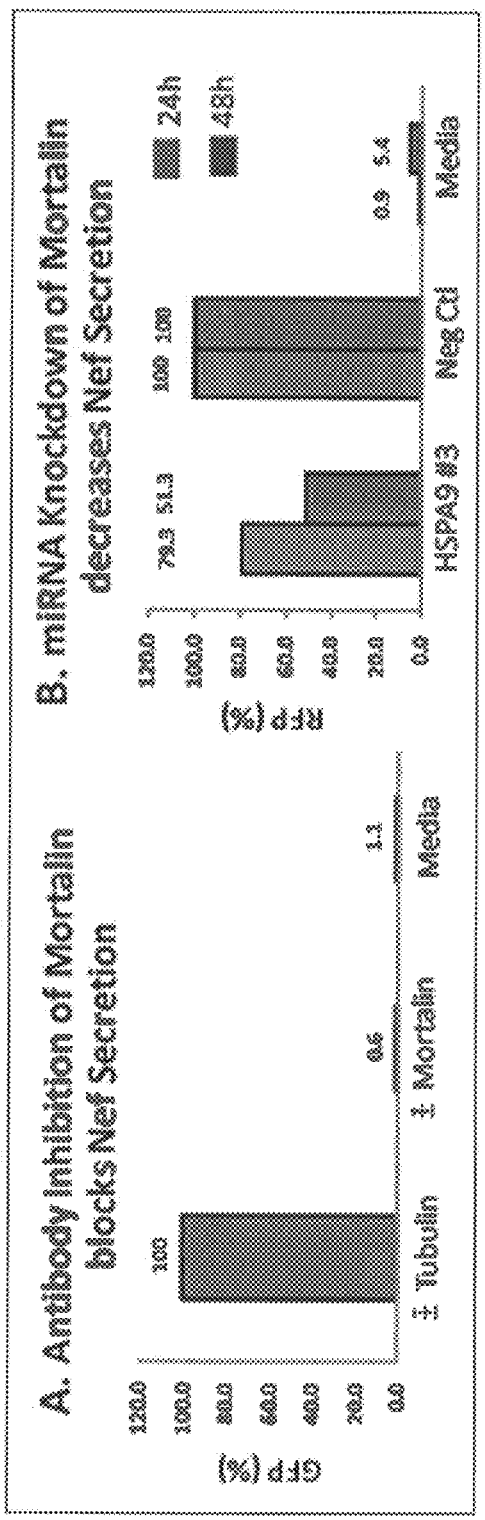
FIG. 4 is a composite of diagrams showing that knockdown of mortalin results in decreased Nef secretion. Panel A: NefGFP and either anti-tubulin antibody, anti-Mortalin antibody or no antibody were cotransfected into Jurkat cells by Chariot. At 48 hr post-transfection, green fluorescence protein (GFP) was assayed in the supernatant as a measure of Nef-induced secretion. Panel B: NefRFP and either anti-Mortalin RNAi or a negative control RNAi, or medium only were cotransfected into Jurkat cells. At 24 and 48 hr post-transfection, red fluorescence protein (RFP) was assayed in the supernatant as a measure of Nef-induced secretion.
Figure 5:
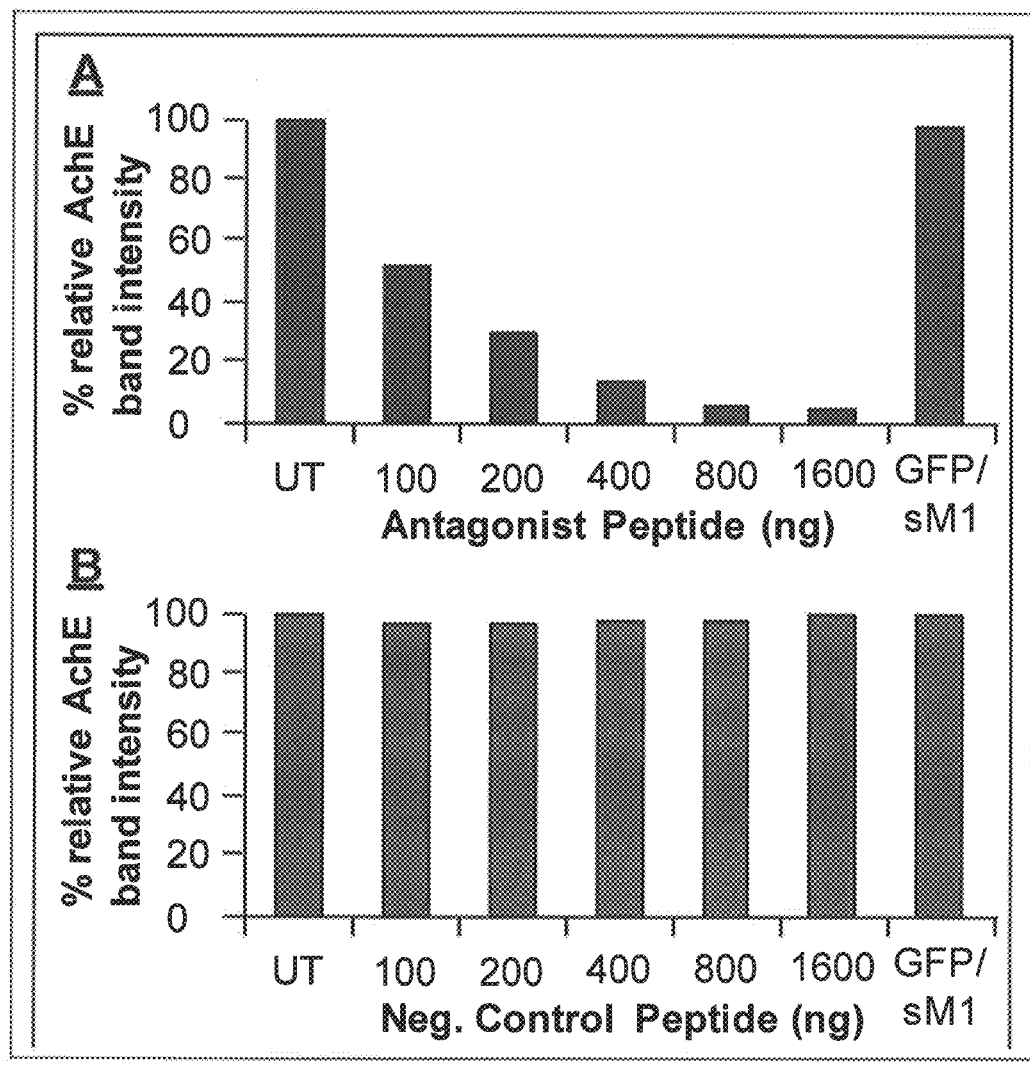
FIG. 5 is a composite of diagrams showing that the SMRwt peptide disrupts tumor exosome release. MDA-MB-231 breast cancer cells were treated with increasing concentrations of the antagonist peptide (panel A), or negative control peptide (panel B). Extracellular AchE was analyzed by Western as a marker for tumor exosome release. sM1 is a random peptide.

Both antibody and miRNA knockdown experiments (FIG. 4) confirmed that blocking Mortalin in Nef transfected cells blocks Nef-containing exosome secretion, and disrupts Mortalin/Nef interactions which occur through the SMR domain. Thus, the SMRwt peptide directly interacts with Mortalin and disrupts its ability to interact with viral Nef. It was also found that the antimicrobial disrupts non-Nef exosomal secretion driven wholly by the cellular machinery in an examination of its effect on tumor exosome release from several tumor cell lines (FIG. 5).

Based on this structural similarity between Mortalin and Dnak, the SMRwt peptide would likely interact with Dnak, and disrupt function(s) of DnaK. This data suggests that the SMRwt peptide can be a new therapeutic agent that exploits the role of Dnak in secretory and/or growth processes.

Example 2: SMRwt Disrupts Growth and Survival of Drug-Resistant Bacteria

Figure 6:
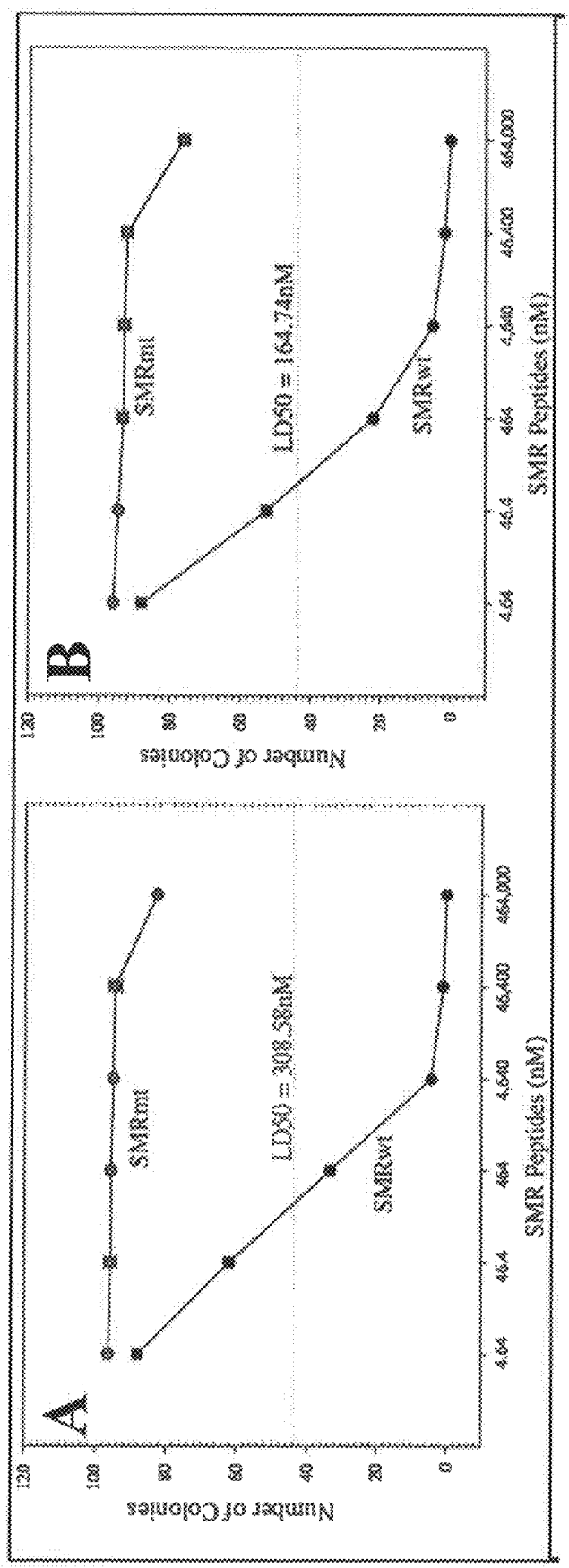
FIG. 6. SMRwt peptide disrupts drug-resistant growth/survival. $E.\ coli$ ($2 \times 10^6$) transformed with pUC18 were grown in the presence of various concentrations (x-axis) of either the antimicrobial peptide (SMRwt) or negative control (SMRmut) for 6 hrs. The resultant bacteria were plated on LB plates+KAN (kanamycin; panel A), or +AMP (ampicillin; panel B). The colonies were counted (y-axis) and the data was plotted as a function of peptide dosage. The LD50 (thin dotted line) is shown for SMRwt antimicrobial peptide in the presence of each bacterial resistance gene.

To examine the effects of SMRwt peptide or SMRmut (mutant) peptide on bacterial survival/growth in the presence of drug-resistant bacteria, *E. coli* (2×106) were transformed with pUC-4K (KAN+) or with pUC18 (AMP+) and grown in the presence of various concentrations (x-axis) of either the antagonist (SMRwt) or the negative control (SMRmut) for 6 hrs (FIG. 6). Briefly, bacterial colonies transformed with pUC18 plasmid containing the ampicillin resistance gene, or pUC4K containing the kanamycin resistance gene were incubated in triplicate at 200-250 rpm at 30° C. The OD at 600 nm was read and adjusted the OD to 0.001 (~106 cells) by adding LB broth. The bacteria were kept on ice to prevent further growth and change of the OD. 10 microliters of peptide stock (10 µg/µl) was added to 90 µl of diluted bacterial solution (final concentration, 1 mg peptide/ml bacterial suspension) in a sterile 2 ml eppendorf tube. The peptides must be so diluted that the final concentration of DMSO is not more than 5%. The negative control contains 5% DMSO. The tubes were incubated at 30° C. while shaking (200 rpm) for various time periods (0,1,3,6,12,24 hours). At each time point, 10 µl of sample from each condition/tube was removed and "dropped" onto the LB agar plate containing suitable antibiotic. Each plate was divided into 4 sections: (i) Negative control—Bacteria exposed to diluent (5% DMSO); (ii) Negative control—Bacteria exposed to diluent without DMSO); (iii) SMRwt—Bacteria exposed to wild type wtSMR peptide antagonist; and (iv) SMRmut—Bacteria exposed to the mutant SMR peptide. Each experiment is performed in triplicate (i.e. on three different plates). After incubating overnight at 30° C., the number of colonies (in each 'drop') on the plate was counted, adjusted for the dilution factor (as above). The results were presented as the number of colonies/ml.

FIG. 6 shows the number of bacteria colonies on LB+KAN (kanamycin) plates (panel A), or LB+AMP (ampicillin) plates (panel B). The data was plotted as a function of peptide dosage. The LD50 (thin dotted line) or MBC50 (minimal bactericidal concentration that kills 50% of the bacteria) is shown for each bacteria/resistance gene.

In the presence of KAN (FIG. 6, panel A) or AMP (FIG. 6, panel B), SMRwt negatively affected bacterial survival after 6 hrs of growth at all SMRwt concentrations tested in a dose-dependent manner. In the presence of KAN or AMP, the MBC50 was about 308.6 nm or 164.7 nm, respectively. In contrast, in the presence of KAN, SMRmut had no effect at SMRmut concentrations up to 150-fold higher than the MBC50 for SMRwt (FIG. 6, panel A). Similarly, in the presence of AMP, SMRmut had virtually no effect at SMRmut concentrations up to 282-fold higher than the MBC50 for SMRwt (FIG. 6, panel B). The antibiotic-dependent differences in MBC50 suggest differences in efficacy for reducing resistance to AMP vs. KAN, which are to be expected given the different modes of action for KAN and AMP.

Example 3: SMRwt Affects Bacterial Growth Independent of Drug Resistance

Figure 7:
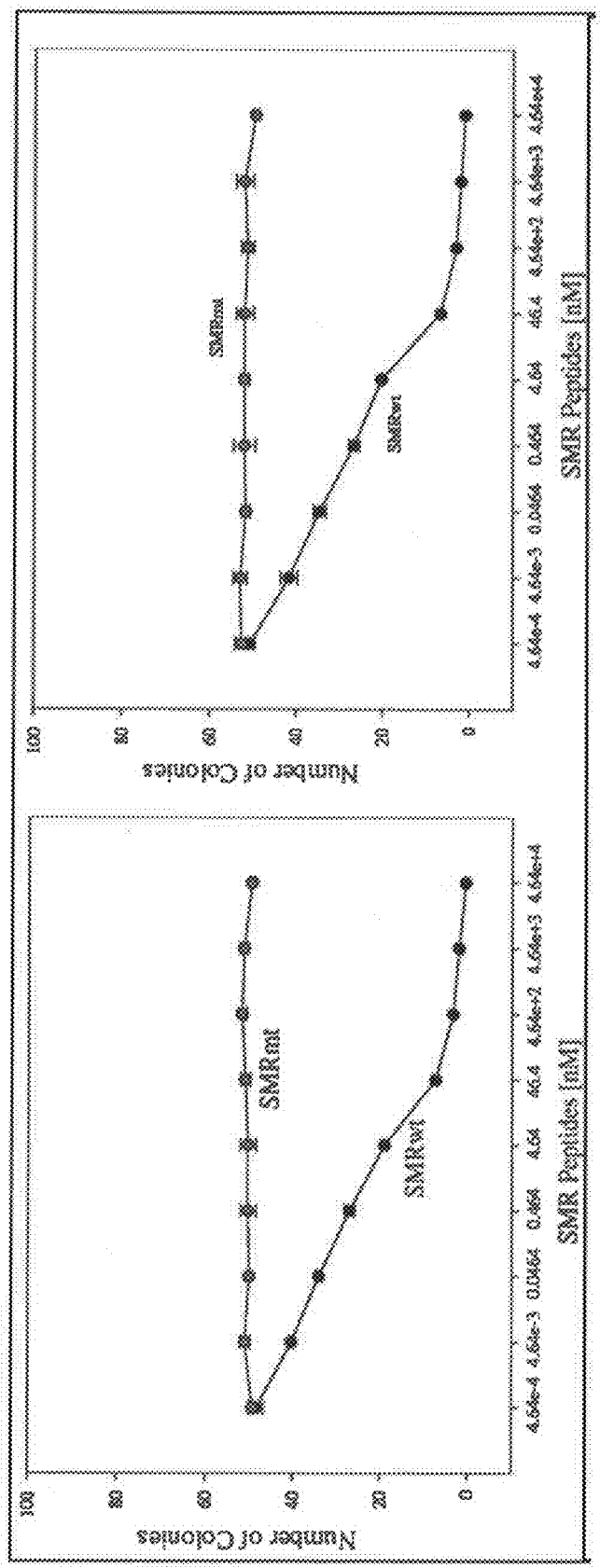
FIG. 7. SMRwt antimicrobial peptide disrupts bacterial growth/survival. $E.\ coli$ ($2 \times 10^6$) transformed with pUC-4K (KAN+)(panel A) or pUC18 (AMP+)(panel B) were grown in L-broth in the presence of various concentrations (x-axis) of either the antagonist (SMRwt) or the negative control peptide (SMRmut) for 12 hrs. The resultant bacteria were plated on antibiotic free LB plates (pUC-4K; panel A), or pUC18; panel B). The colonies were counted (y-axis) and the data was plotted as a function of peptide dosage.

To examine the effects of SMRwt peptide on bacterial survival/growth in the absence of antibiotics, *E. coli* (2×106) transformed with pUC-4K (KAN+) or with pUC18 (AMP+) were grown in the presence of various concentrations (x-axis) of either the antagonist (SMRwt) or the negative control (SMRmut) for 12 hrs (FIG. 7). The resultant pUC-4K (KAN+)-transformed *E. coli* (panel A) or pUC18 (AMP+)-transformed *E. coli* were plated on drug-free LB plates for 12 hours (panel B). Colonies were counted (y-axis) and the data was plotted as a function of peptide dosage in these two non-stressed drug-free environments.

The results in FIG. 7 show that even in these two non-stressful, drug free environments, there was a dose-responsive effect of SMRwt on survival/growth of the cells. The minimum bactericidal concentration (MBC50) for the two plasmid-containing bacteria exposed as described above for 6 hours, and 12 hours are shown in Table 1. As evidenced by the lower MBCs in the antibiotic-free conditions, the SMRwt peptides were significantly more bactericidal under the non-stressed, antibiotic-free conditions.

TABLE 1

| AMPICILLIN/pUC18 | | KANAMYCIN/pUC18 or pUC4-K | |
| --- | --- | --- | --- |
| Grown on Ampicillin plates | | Grown on Kanamycin plates | |
| 6 hour exposure | MDC50 = 164.74 nM | 6 hour exposure | MDC50 = 308.58 nM |
| Plated on antibiotic plates | MDC50 = 0.355 µg/ml | Plated on antibiotic plates | MDC50 = 0.865 µg/ml |
| Grown on L-Plates | | Grown on L-Plates | |
| 12 hr exposure | MCD50 = 1.565 nM | 12 hr exposure | MDC50 = 2.03 nM |
| Plated on LB plates | MDC50 = 2.1 ng/ml | Plated on LB plates | MDC50 = 4.75 ng/ml |

Figure 8:
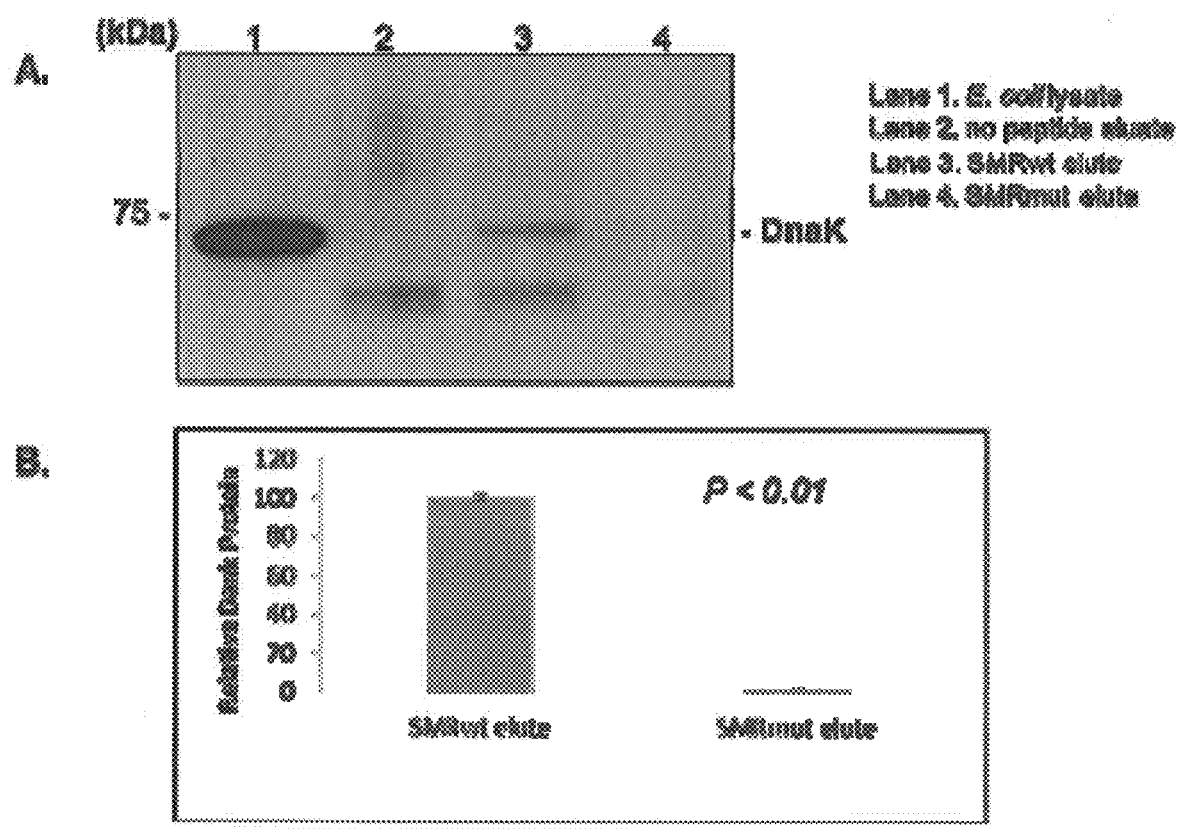
FIG. 8. Interaction between the antimicrobial peptide and DnaK. $E.\ coli$ was grown in media without antibiotics. The cells were lysed, and the resultant lysate screened by immunoprecipitation with ANTI-FLAG® M2 Affinity Gel plus either the SMRwt, SMRmut peptide, or in the absence of both peptides. Bound proteins/peptides were eluted, the eluted proteins separated by SDS-PAGE. Panel A depicts a Western blot analysis performed using mouse monoclonal Dnak antibody (1:1000) and Thermo Scientific Immunopure® Goat Anti-Mouse IgG (H+L), Peroxidase Conjugated secondary antibody (1:2000). Lane 1, $E.\ coli$ lysate; lane 2, no peptide eluate; lane 3, SMRwt eluate; lane 4, SMRmut eluate. Panel B shows a comparison between the amount of Dnak protein co-eluting with the SMRwt peptide in comparison to SMRmut peptide. This assay shows that the interaction with Dnak is specific for the SMRwt peptide; no detectable Dnak protein was eluted with SMRmut peptide.

Example 4: Antimicrobial Peptide Nef-SMR Forms a Complex with *E. coli* Dnak Protein FIG. 8 shows an immunoprecipitation analysis demonstrating an interaction between SMR interacts and *E. coli* DnaK. INVITROGEN™ MAX Efficiency® STBL2TM Competent (*E. coli*) cells were grown overnight at 30° C. in LB Broth without antibiotics and lysed with Novagen® BUGBUSTER™ Protein Extraction Reagent. 1 mg of *E. coli* lysate was incubated overnight at 4° C. with 20 µL of Sigma® ANTI-FLAG® M2 Affinity Gel in the absence of peptide (lane 2) or in the presence of 1 µg of either the SMRwt (wide-type) peptide (lane 3) or SMRmut (mutant) peptide (lane 4). Following three washes with TBS (50 mM Tris HCl, 150 mM NaCl, pH 7.4), bound proteins/peptides were eluted from the beads by competition with Sigma-Aldrich® 3X FLAG® Peptide.

The eluted proteins/peptides were separated by SDS-PAGE and subjected to Western analysis using Abcam® Mouse monoclonal Dnak antibody [8E2/2] (Primary; 1:1000) and Thermo Scientific Immunopure® Goat Anti-Mouse IgG (H+L), Peroxidase Conjugated antibody (Secondary: 1:2000). The results of this analysis show that the SMRwt peptide forms a complex with the Dnak protein, while the negative control peptide exhibits negligible binding.

Example 5: SMRwt Peptide Inhibits Biofilm Formation by Methicillin-Resistant *Staphylococcus aureus* SCO1 (MRSA), *Vibrio cholerae* C7258 and *Escherichia coli* 042

Methods

Figures 9, 10:
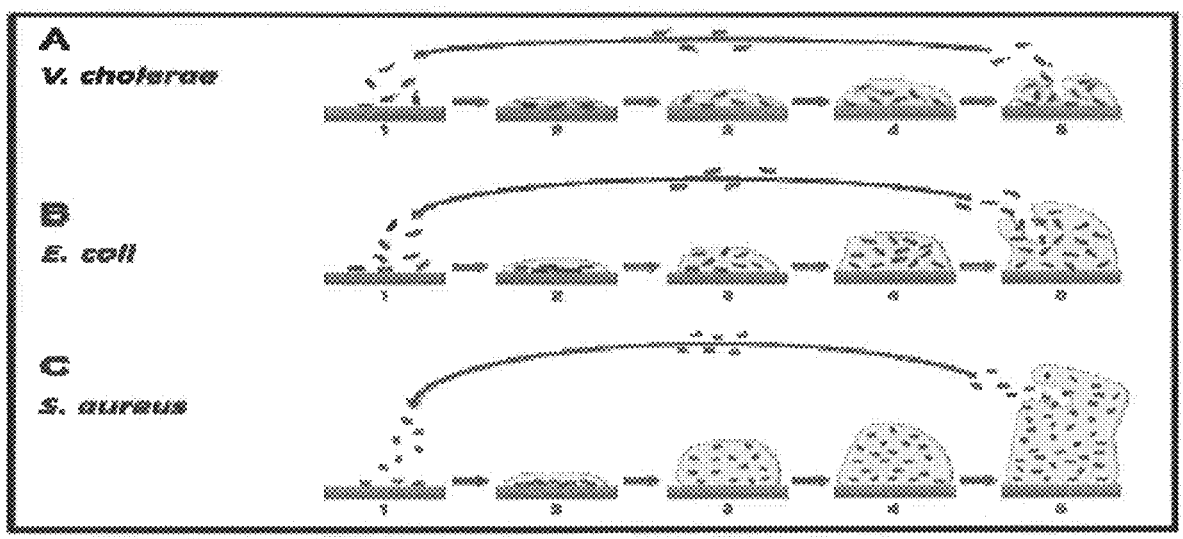
FIG. 9 shows synthetic SMR(wt)-CPP (tat)-(SEQ ID NO: 9) and SMR(mut)-CPP (tat) (SEQ ID NO: 11) peptide antagonists for evaluating inhibition of biofilm formation in Gram-negative and Gram-positive bacteria.
FIG. 10 shows bacteria biofilm formation process schematic. Bacteria Biofilm Formation Process Schematic: 1. Association: bacteria attach plate surface or various other host cells surfaces; 2. Cell-cell Adhesion: within hours, bacteria loosely binds to the pellicle; 3. Proliferation: bacteria spreads throughout the medium and begins to multiply; 4. Growth or maturation: the biofilm develops: S. Release: large biofilm aggregates detach forming flocks and planktonic bacterial cells migrate from the mature biofilm into a primitive circulatory system, where adherence to distal tissue and formation of a nascent biofilm can occur to repeat the cycle. (A) $V.\ cholera$; and (B) $E.\ coli$; and (C) $S.\ aureus$.
Figure 11:
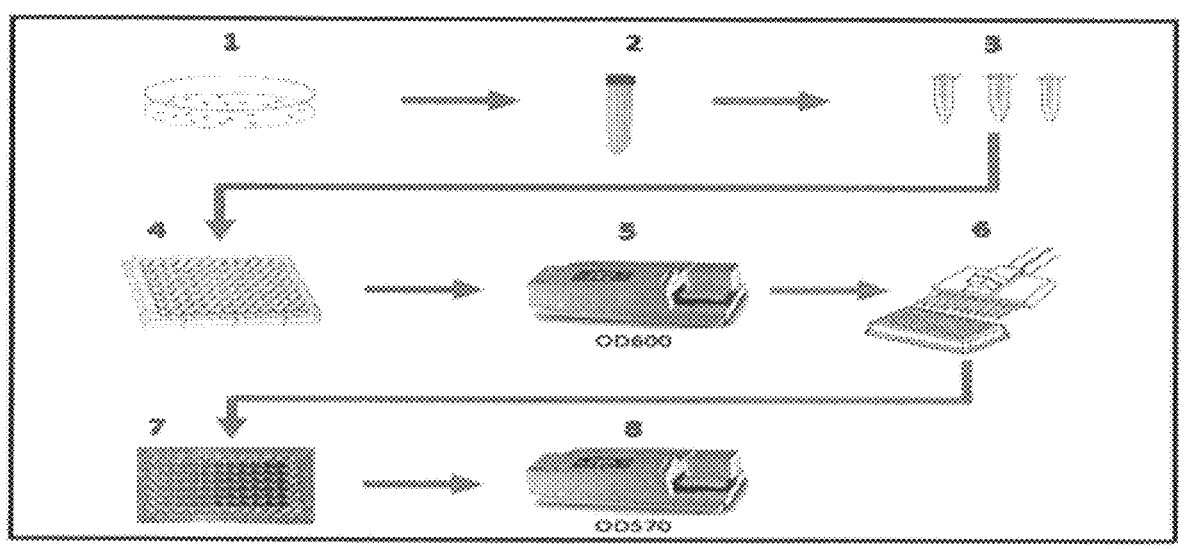
FIG. 11 shows schematic of a crystal violet assay used to evaluate biofilm formation and measurement. Biofilm Formation and Measurement Procedures by Crystal Violet Assay: (1) incubate bacteria in agar plate; (2) single colony was transferred to fresh medium and incubated for overnight; (3) cultures were diluted 1:50 into fresh medium and (4) was dispensed into 96 well plate and incubated for overnight; (5) detection of bacteria growth ability, the OD at 600 nm was determined by the SpectraMax M5 Microplate Reader (6) washed by 1×PBS; (7) stained with crystal violet; (8) detection of biofilm, the OD at 570 nm was determined by the SpectraMax M5 Microplate Reader.

FIG. 9 shows the sequence of an HIV-I Nef SMRwt-CPPtat peptide having the sequence of VGFPVAAVGFPVGRKKRRQRRRPPQ (SEQ ID NO: 9), which is the peptide of SEQ ID NO: 3 with an HIV-Tat cell penetrating peptide (CPP) domain (i.e., GRKKRRQRRRPPQ, SEQ ID. NO. 8) at the C-terminal end, and HIV-1 Nef SMRmut-CPPtat peptide (i.e., AGFPVAAAGFPVGRKKRRQRRRPPQ, SEQ ID NO:11, which is a peptide containing an HIV-1 Nef SMRmut (i.e., AGFPVAAAGFPV, SEQ ID NO: 10) with the HIV-Tat CPP domain (SEQ ID NO: 8) for use as a negative control. The SMRwt-CPP and SMRmut-CPP peptides were custom made by InnoPep Inc. (San Diego, CA).

Bacterial strains evaluated for biofilm formation included (1) the Gram-negative *Vibrio cholerae* C7258 strain (A. J. Silva et al., *J. Bact.*, 190 (22):7335-7345 (Nov. 2008); J. C. Ayala et al., *Genomics data* 5, pp. 147-150, (2015)); (2) the Gram-negative *Escherichia coli* 042 strain (Taxonomy ID: 216592, R. R. Chaudhuri et al, *PLOS One*, 5(1): e8801 (Jan. 20, 2010), and (3) the Gram-positive *Staphylococcus aureus* SCO1 strain (ATCC 12228, S. Sarkar et al., *PLos One*, 10(2): e0117613 (2015). The *Vibrio cholerae, Escherichia coli* and *Staphylococcus aureus* strains and plasmids are listed in the references cited in Table 2.

TABLE 2

| Bacteria | Strains | Description | References |
| --- | --- | --- | --- |
| *Vibrio cholera* | C7258 | Wild-type, El Tor, Ogawa, from Peru, 1991 | Benitez, J. A., et al., Infection and Immunity, February 1999, p. 539-545. |
| *Escherichia coli* | O42 | Prototype EAEC strain (044:H18) lac+, Sm Tc Cm | Harrington, S. M., et al., Infection and Immunity, June 2009, p. 2465-2473. |
| *Staphylococcus aureus* | SC01 | Wild-type, cna+ | Beenken, K. E., et al., Infection and Immunity, July 2003, p. 4206-4211. |

Figure 12:
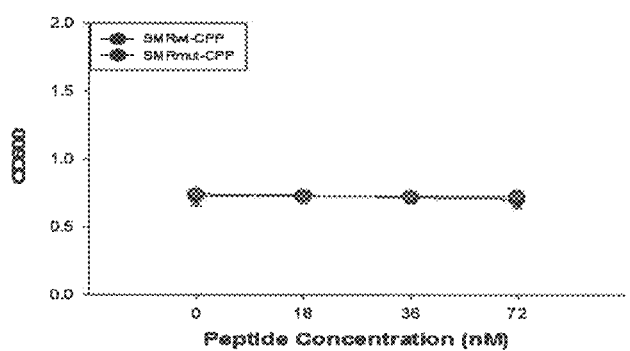
FIG. 12 shows SMR(wt)-CPP (tat) peptide-mediated dose-response inhibition of biofilm formation by *V. cholerae*. SMR(mut)-CPP (tat) peptide was used as a negative control.
Figure 12:
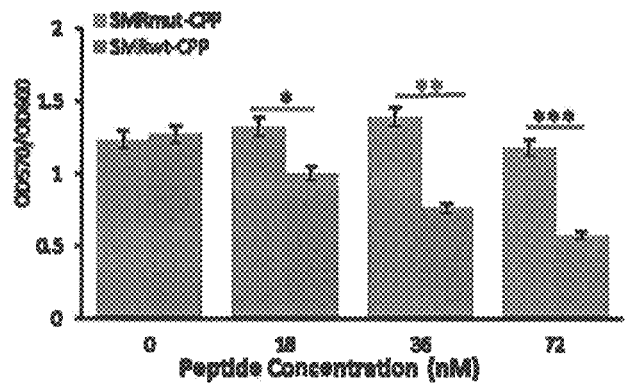
Figure 13:
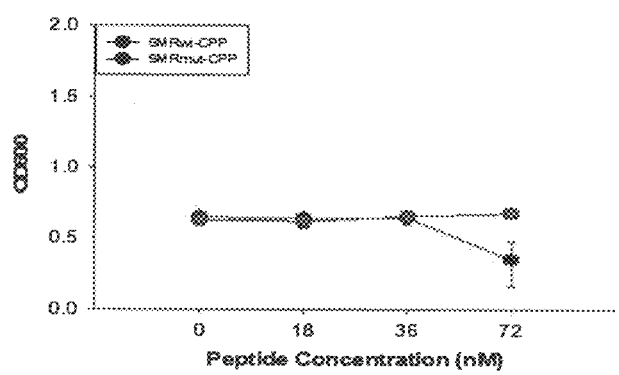
FIG. 13 shows SMR(wt)-CPP (tat) peptide-mediated dose-response inhibition of biofilm formation by *E. coli*. SMR(mut)-CPP (tat) peptide was used as a negative control.
Figure 13:
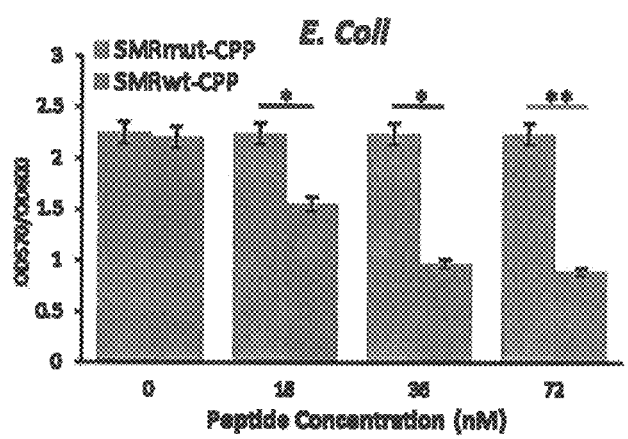
Figure 14:
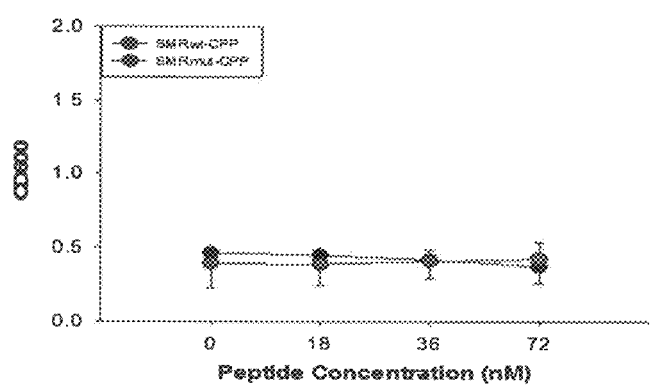
FIG. 14 shows SMR(wt)-CPP (tat) peptide-mediated dose-response inhibition of biofilm formation by *S. aureus*. SMR(mut)-CPP (tat) peptide was used as a negative control.
Figure 14:
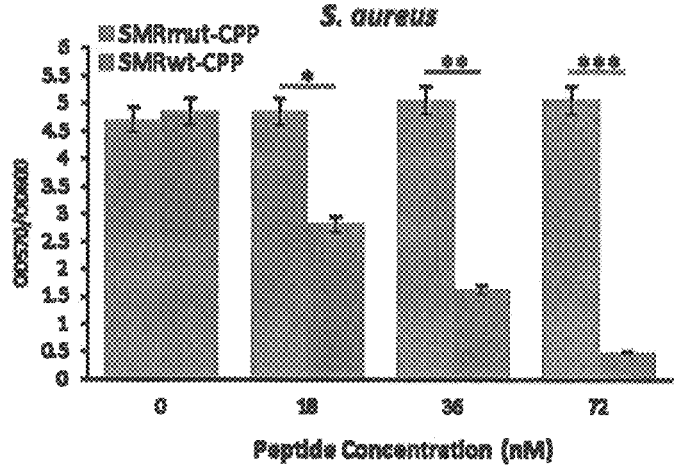
Figure 15:
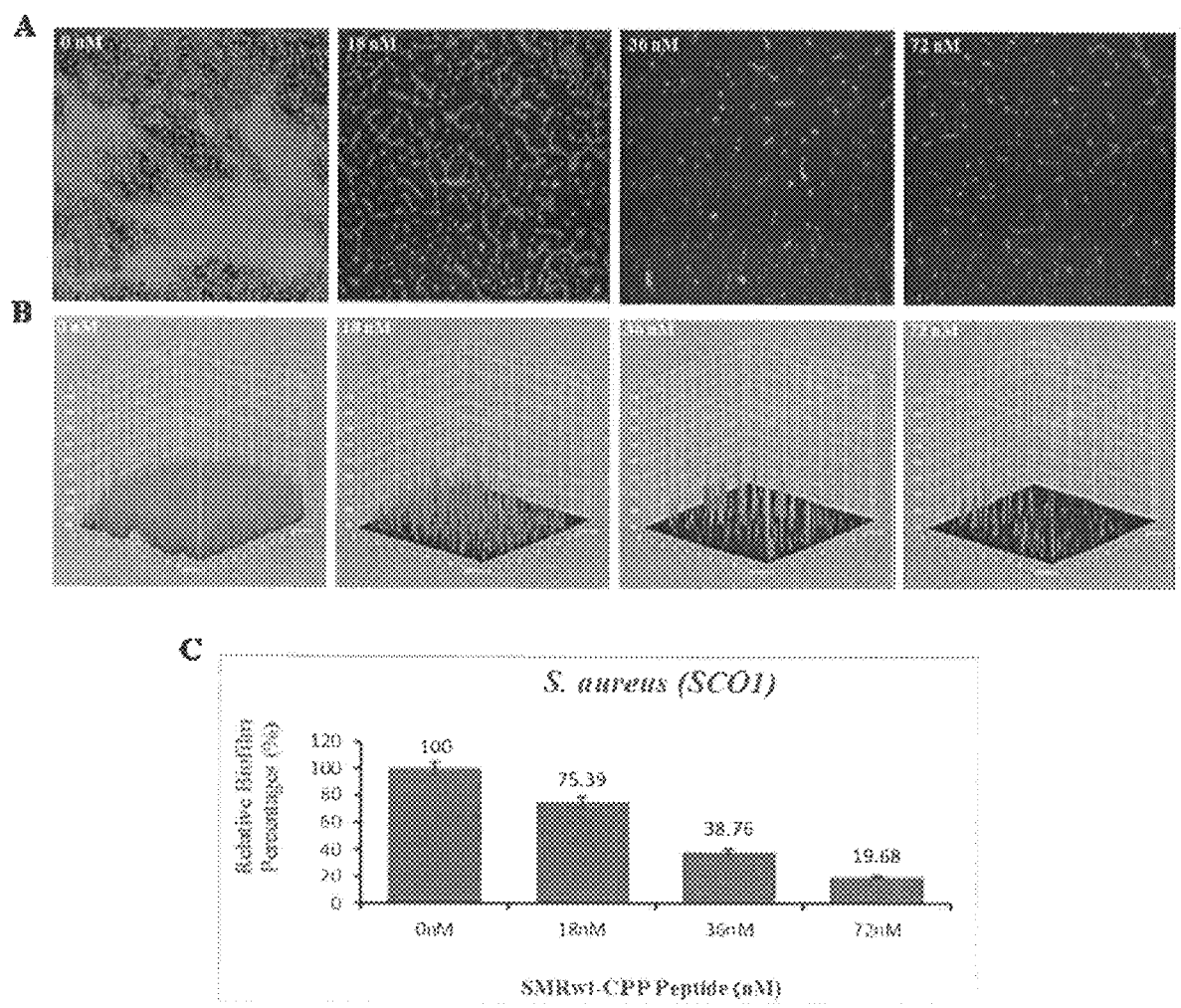
FIG. 15 shows SMR(wt)-CPP (tat) peptide-mediated dose-response inhibition of biofilm formation by *Staphylococcus aureus*. Strain SCO1 was grown in LB medium at 37° C. to stationary phase. The cultures were diluted 100 fords in fresh medium and biofilm allowed to develop under static conditions for 24 h in Mat Tek glass bottom culture plates. Biofilm formation was stained with SYTO9 and observed by Leico confocal microscopy and three-dimensional (3D) views of *S. aureus* and measured using the ImageJ. (A) Confocal images, (B) 3D images, and (C) bar graphs showing the inhibit effect of biofilm formation. Error bars represent the mean±SD of two independent experiments. Asterisks (*) indicate significant differences (p≤0.05) relative to negative control * p<0.01 (18 nM), ** p<0.001 (36 nM, 72 nM) in SMR-CPP peptide treatment. Each value represents the mean of three independent experiments. Error bars denote the standard deviation (STDEV).
Figure 16:
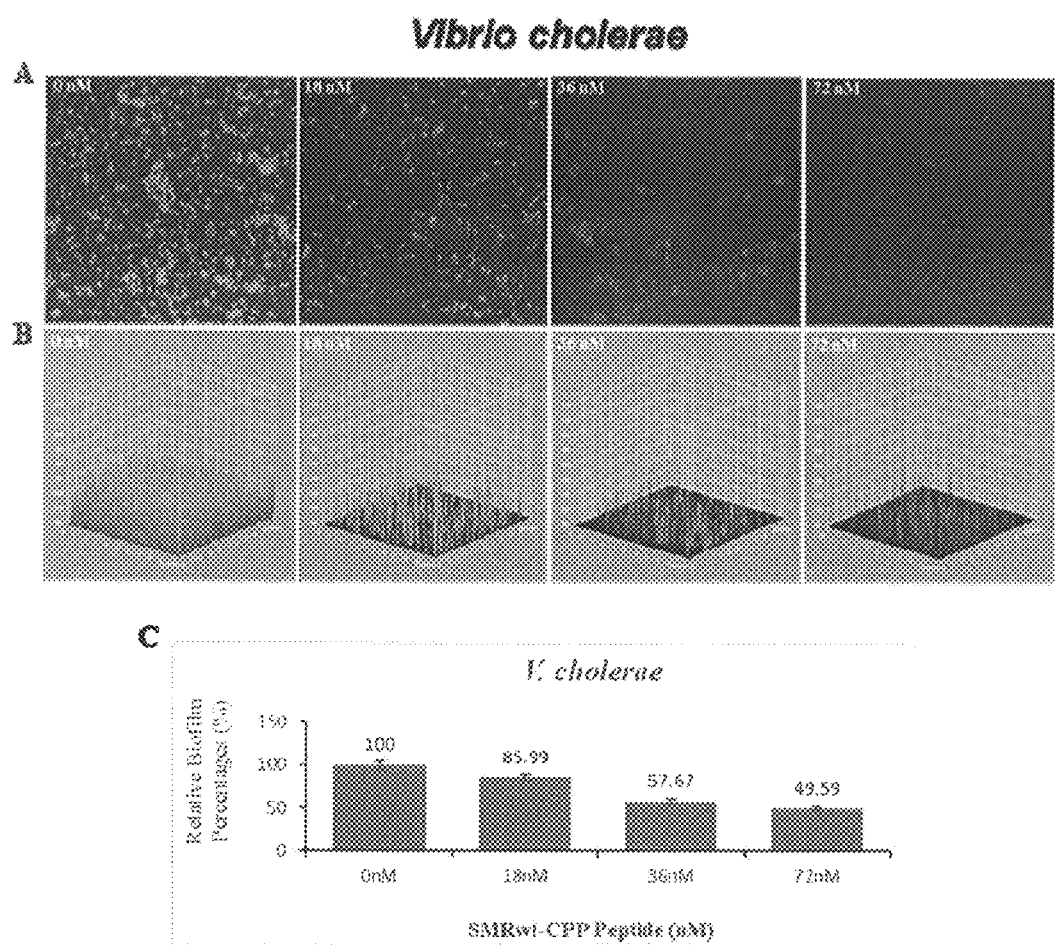
FIG. 16 shows SMR(wt)-CPP (tat) peptide-mediated dose-response inhibition of biofilm formation by *Vibrio cholerae*. Strain *V. cholerae* C7258 was grown in LB medium at 30° C. to stationary phase. The cultures were diluted 100 fords in fresh medium and biofilm allowed to develop under static conditions for 24 h in Mat Tek glass bottom culture plates. Biofilm formation was stained with SYTO9 and observed by Leico confocal microscopy and three-dimensional (3D) views of *V. cholerae* and measured using the ImageJ. (A) Confocal images, (B) 3D images, and (C) bar graphs showing the inhibit effect of biofilm formation. Error bars represent the mean±SD of two independent experiments. Asterisks (*) indicate significant differences (p≤ 0.05) relative to negative control * p<0.01 vs 18 nM, 36 nM and 72 nM SMRwt-CPP peptide treatment. Each value represents the mean of three independent experiments. Error bars denote the standard deviation (STDEV).

The *Vibrio cholerae, Escherichia coli* and *Staphylococcus aureus* strains were treated with SMRwt-CPP and SMRmut-CPP peptides and screened for inhibition of their biofilm-forming capacity using microtiter plate (MtP) methods (FIGS. 12-14 (crystal violet assays)) and confocal microscopy (FIGS. 15-16 (intensity count on confocal images).

These results confirmed the ability of SMRwt-CPP peptide to inhibit biofilm inhibition in both Gram-negative and Gram-positive bacterial strains. As shown in FIGS. 12-14, SMRmut-CPP peptide had no significant effect on inhibiting biofilm formation.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the object of the present application, and it is not intended to detail all those obvious modifications and variations of it which will become apparent to the skilled worker upon reading the description. It is intended, however, that all such obvious modifications and variations be included within the scope of the present application, which is defined by the following claims. The aspects and embodiments are intended to cover the components and steps in any sequence which is effective to meet the objectives there intended, unless the context specifically indicates the contrary.

What is claimed is:

1. A biologically compatible anti-biofilm coating or impregnator for detaching or dispersing gram-positive or gram-negative bacterial biofilms;
   wherein the anti-biofilm coating or impregnator is selected from the group consisting of paint, glue, or cement;
   wherein the anti-biofilm paint, glue, or cement comprises a gram-positive or gram-negative anti-bacterial secretion modifying region (SMR) peptide;
   wherein the SMR peptide consists of the amino acid sequence of SEQ ID NO: 9;
   wherein the anti-biofilm paint, glue, or cement further comprises the SMR peptide SEQ ID NO: 9 in an effective concentration to inhibit biofilm formation by at least greater than 80% by any gram-positive or gram-negative bacteria;
   and wherein the anti-biofilm coating or impregnator does not contain a bacterial biofilm-degrading enzyme.

2. The biologically compatible anti-biofilm coating or impregnator of claim 1, further comprising one or more other antimicrobial peptides (AMPs), antibiotics, matrix-inhibiting compounds, matrix-disaggregating compounds, quorum sensing inhibitors, or a combination thereof.

3. The biologically compatible anti-biofilm coating or impregnator of claim 1, wherein the coating is a marine coating.

4. The biologically compatible anti-biofilm coating or impregnator of claim 1, wherein the paint does not contain heavy metals.

5. A biologically compatible item comprising the biologically compatible anti-biofilm coating or impregnator of claim 1, where the item is selected from the group consisting of a medical device, medical instrument, medical implement, medical prosthetic, and medical implantable device.

* * * * *